US010335454B2

(12) United States Patent
Coates et al.

(10) Patent No.: US 10,335,454 B2
(45) Date of Patent: Jul. 2, 2019

(54) COMBINATION AND USE

(71) Applicant: HELPERBY THERAPEUTICS LIMITED, London, Greater London (GB)

(72) Inventors: Anthony Coates, London (GB); Yanmin Hu, London (GB)

(73) Assignee: HELPERBY THERAPEUTICS LIMITED, London, Greater London (GB)

( * ) Notice: Subject to any disclaimer, the term of this patent is extended or adjusted under 35 U.S.C. 154(b) by 0 days.

(21) Appl. No.: 15/537,007

(22) PCT Filed: Dec. 18, 2015

(86) PCT No.: PCT/GB2015/054069
§ 371 (c)(1),
(2) Date: Jun. 16, 2017

(87) PCT Pub. No.: WO2016/097754
PCT Pub. Date: Jun. 23, 2016

(65) Prior Publication Data
US 2017/0348383 A1 Dec. 7, 2017

(30) Foreign Application Priority Data

| Dec. 18, 2014 | (GB) | 1422670.8 |
| Jan. 8, 2015 | (GB) | 1500278.5 |
| Dec. 11, 2015 | (GB) | 1521901.7 |

(51) Int. Cl.
| *A61K 31/05* | (2006.01) |
| *A61K 38/12* | (2006.01) |
| *A61K 31/145* | (2006.01) |
| *A61K 31/216* | (2006.01) |
| *A61K 31/382* | (2006.01) |
| *A61K 31/405* | (2006.01) |
| *A61K 31/416* | (2006.01) |
| *A61K 31/428* | (2006.01) |
| *A61K 31/616* | (2006.01) |
| *A61K 31/135* | (2006.01) |
| *A61K 31/192* | (2006.01) |
| *A61K 31/196* | (2006.01) |
| *A61K 31/5415* | (2006.01) |

(52) U.S. Cl.
CPC .............. *A61K 38/12* (2013.01); *A61K 31/05* (2013.01); *A61K 31/135* (2013.01); *A61K 31/145* (2013.01); *A61K 31/192* (2013.01); *A61K 31/196* (2013.01); *A61K 31/216* (2013.01); *A61K 31/382* (2013.01); *A61K 31/405* (2013.01); *A61K 31/416* (2013.01); *A61K 31/428* (2013.01); *A61K 31/5415* (2013.01); *A61K 31/616* (2013.01); *Y02A 50/401* (2018.01); *Y02A 50/404* (2018.01); *Y02A 50/406* (2018.01); *Y02A 50/469* (2018.01); *Y02A 50/473* (2018.01); *Y02A 50/479* (2018.01); *Y02A 50/481* (2018.01); *Y02A 50/483* (2018.01)

(58) Field of Classification Search
None
See application file for complete search history.

(56) References Cited

U.S. PATENT DOCUMENTS

| 5,679,665 A * | 10/1997 | Bergamini | A61K 38/04 514/171 |
| 6,974,585 B2 | 12/2005 | Askill | |
| 2013/0243886 A1 * | 9/2013 | Hu | A61K 31/138 424/649 |

FOREIGN PATENT DOCUMENTS

| GB | 1276839 A | 6/1972 |
| WO | 9510999 A1 | 4/1995 |
| WO | 0028074 A1 | 5/2000 |
| WO | 2005014585 A1 | 2/2005 |
| WO | 2006048747 A1 | 5/2006 |
| WO | 2012032360 A2 | 3/2012 |
| WO | 2014052836 A2 | 4/2014 |

(Continued)

OTHER PUBLICATIONS

J. Alexander et al., "Investigation of (Oxodioxolenyl)methyl Carbamates as Nonchiral Bioreversible Prodrug Moieties for Chiral Amines", J. Med. Chem., 1996, vol. 39, No. 2, pp. 480-486 (7 pages).
S. M. Berge et al., "Pharmaceutical Salts", Journal of Pharmaceutical Sciences, Jan. 1977, vol. 66, No. 1, pp. 1-19 (20 pages).
A. Coates et al., "The future challenges facing the development of new antimicrobial drugs", Nature Reviews (Drug Discovery), Nov. 2002, vol. 1, pp. 895-910 (18 pages).
P. Davey et al., "Tolerance of *Pseudomonas aeruginosa* to killing by ciprofloxacin, gentamicin and imipenem in vitro and in vivo", Journal of Antimicrobial Chemotherapy, 1988, vol. 21(4), pp. 395-404 (10 pages).

(Continued)

*Primary Examiner* — Christina Bradley
(74) *Attorney, Agent, or Firm* — Sughrue Mion, PLLC

(57) ABSTRACT

The present invention relates to the use of one or more compounds selected from the following: caffeic acid, thymol, aspirin, benzydamine hydrochloride, diclofenac sodium, flurbiprofen, ibuprofen, indomethacin, trifluoperazine hydrochloride, chlorprothixene hydrochloride, triflupromazine hydrochloride, suloctidil, thioridazine hydrochloride, dichlorophen, saccharin and piroxicam, in combination with a polymyxin selected from colistin or polymyxin B or a pharmaceutically acceptable derivative thereof, for use in the treatment of a microbial infection, and in particular for killing clinically latent microorganisms associated with microbial infections. The invention also provides a combination comprising suloctidil or a pharmaceutically acceptable derivative or prodrug thereof, and a polymyxin selected from polymyxin E and polymyxin B or a pharmaceutically acceptable derivative thereof. This combination is particularly useful for the treatment and/or prevention of microbial infections.

14 Claims, 21 Drawing Sheets
(21 of 21 Drawing Sheet(s) Filed in Color)

(56) References Cited

FOREIGN PATENT DOCUMENTS

| WO | 2014134005 A2 | 9/2014 |
| WO | 2014147405 A1 | 9/2014 |

OTHER PUBLICATIONS

A. Doléans-Jordheim et al., "Zidovudine (AZT) has a bactericidal effect on enterobacteria and induces genetic modifications in resistant strains", Eur. J. Clin. Microbiol. Infect. Dis., 2011, vol. 30, pp. 1249-1256 (8 pages).

C.A. Fux et al., "Survival strategies of infectious biofilms", Trends in Microbiology, Jan. 2005, vol. 13(1), pp. 34-40 (7 pages).

R. D. Gonzales et al., "Infections due to vancomycin-resistant *Enterococcus faecium* resistant to linezolid", The Lancet, Apr. 14, 2001, vol. 357(9263), p. 1179 (1 page).

K. H. Groicher et al., "The *Staphylococcus aureus* lrgAB operon modulates murein hydrolase activity and penicillin tolerance", Journal of Bacteriology, Apr. 2000, vol. 182, No. 7, pp. 1794-1801 (8 pages).

Y. Hu et al., "Increased levels of sigJ mRNA in late stationary phase cultures of *Mycobacterium tuberculosis* detected by DNA array hybridisation", FEMS Microbiology Letters, 2001, vol. 202(1), pp. 59-65 (7 pages).

Y. Hu et al., "Detection of mRNA transcripts and active transcription in persistent *Mycobacterium tuberculosis* induced by exposure to rifampin or pyrazinamide", Journal of Bacteriology, Nov. 2000, vol. 182, No. 22, pp. 6358-6365 (8 pages).

Y. Hu et al., "Enhancement by novel anti-methicillin-resistant *Staphylococcus aureus* compound HT61 of the activity of neomycin, gentamicin, mupirocin and chlorhexidine: in vitro and in vivo studies", J. Antimicrob. Chemother., 2013, vol. 68, No. 2, pp. 374-384 (11 pages).

D. Hughes et al., "Carbon starvation of *Salmonella typhimurium* does not cause a general increase of mutation rates", Journal of Bacteriology, Nov. 1997, vol. 179(21), pp. 6688-6691.

J. L. Martinez et al., "Mutation frequencies and antibiotic resistance", Antimicrobial Agents and Chemotherapy, Jul. 2000, vol. 44(7), pp. 1771-1777 (7 pages).

G. Orhan et al., "Synergy Tests by E Test and Checkerboard Methods of Antimicrobial combinations against *Brucella melitensis*", Journal of Clinical Microbiology, Jan. 2005, vol. 43, No. 1, pp. 140-143 (4 pages).

A. L. Spoering et al., "Biofilms and planktonic cells of *Pseudomonas aeruginosa* have similar resistance to killing by antimicrobials", Journal of Bacteriology, Dec. 2001, vol. 183(23), pp. 6746-6751 (6 pages).

B. G. Spratt, "Resistance to antibiotics mediated by target alterations", Science, Apr. 15, 1994, vol. 264(5157), pp. 388-393 (6 pages).

F. Taddei et al., "cAMP-dependent SOS induction and mutagenesis in resting bacterial populations", Proc. Natl. Acad. Sci. USA, Dec. 1995, vol. 92(25), pp. 11736-11740 (5 pages).

S. Tsiodras et al., "Linezolid resistance in a clinical isolate of *Staphylococcus aureus*", The Lancet, Jul. 21, 2001, vol. 358(9277), pp. 207-208 (2 pages).

G. J. Van Asselt et al., "Detection of penicillin tolerance in *Streptococcus pyogenes*", Journal Med. Microbiol., 1993, vol. 38(3), pp. 197-202 (6 pages).

M. E. Falagas et al, "Colistin: The revival of polymyxins for the management of multidrug-resistant gram-negative bacterial infections", Reviews of Anti-Infective Agents, Clinical Infectious Diseases, May 1, 2005, vol. 40, No. 9, pp. 1333-1341, XP009188870 (10 pages).

\* cited by examiner

| | | \multicolumn{12}{c|}{HT0120566} |
|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.58 | 0.51 | 0.52 | 0.52 | 0.52 | 0.52 | 0.52 | 0.52 | 0.53 | 0.53 | 0.53 | 0.54 |
| | 16 | 0.58 | 0.50 | 0.52 | 0.51 | 0.52 | 0.52 | 0.53 | 0.53 | 1.28 | 1.44 | 1.56 | 1.60 |
| | 8 | 0.58 | 0.53 | 0.52 | 0.52 | 0.52 | 0.53 | 0.59 | 1.63 | 1.65 | 1.62 | 1.61 | 1.66 |
| | 4 | 0.58 | 0.52 | 0.52 | 0.52 | 0.53 | 0.53 | 1.73 | 1.71 | 1.72 | 1.66 | 1.63 | 1.75 |
| | 2 | 0.58 | 0.52 | 0.52 | 0.52 | 0.53 | 1.68 | 1.75 | 1.74 | 1.77 | 1.72 | 1.69 | 1.75 |
| | 1 | 0.58 | 0.53 | 0.52 | 0.53 | 1.72 | 1.71 | 1.73 | 1.73 | 1.75 | 1.68 | 1.72 | 1.73 |
| | 0.5 | 0.58 | 0.52 | 0.51 | 1.70 | 1.72 | 1.73 | 1.74 | 1.77 | 1.75 | 1.76 | 1.74 | 1.76 |
| | 0 | 1.81 | 1.78 | 1.74 | 1.77 | 1.79 | 1.79 | 1.78 | 1.77 | 1.78 | 1.77 | 1.76 | 1.77 |

Figure 40

| | | \multicolumn{12}{c|}{HT0121567} |
|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.39 | 0.39 | 0.39 | 0.38 | 0.38 | 0.38 | 0.38 | 0.38 | 0.39 | 0.40 | 0.45 | 0.38 |
| | 16 | 0.39 | 0.39 | 0.39 | 0.39 | 0.39 | 0.39 | 0.39 | 0.38 | 0.40 | 0.45 | 0.47 | 0.38 |
| | 8 | 0.39 | 0.39 | 0.39 | 0.38 | 0.39 | 0.38 | 0.39 | 0.39 | 0.39 | 0.44 | 0.53 | 0.52 |
| | 4 | 0.38 | 0.39 | 0.39 | 0.39 | 0.39 | 0.39 | 0.39 | 0.39 | 0.40 | 0.47 | 0.64 | 0.95 |
| | 2 | 0.39 | 0.39 | 0.39 | 0.39 | 0.39 | 0.39 | 0.39 | 0.39 | 0.77 | 0.74 | 0.74 | 0.72 |
| | 1 | 0.39 | 0.39 | 0.39 | 0.39 | 0.72 | 0.71 | 0.81 | 0.92 | 0.88 | 0.85 | 0.88 | 1.08 |
| | 0.5 | 0.39 | 0.39 | 0.39 | 0.60 | 1.62 | 0.72 | 0.81 | 0.84 | 0.89 | 0.85 | 0.90 | 1.03 |
| | 0 | 0.39 | 0.39 | 0.39 | 0.74 | 1.67 | 0.74 | 0.91 | 0.99 | 1.04 | 1.06 | 1.77 | 1.15 |

Figure 41

| | | \multicolumn{11}{c|}{Colistin} |
|---|---|---|---|---|---|---|---|---|---|---|---|---|
| | | 64 | 32 | 16 | 8 | 4 | 2 | 1 | 0.5 | 0.25 | 0.125 | 0.0625 | 0 |
| HT0120969 | 256 | 0.04 | 0.04 | 0.04 | 0.04 | 0.04 | 0.04 | 0.24 | 0.25 | 0.26 | 0.25 | 0.26 | 0.28 |
| | 128 | 0.04 | 0.04 | 0.04 | 0.04 | 0.09 | 0.28 | 0.35 | 0.46 | 0.49 | 0.50 | 0.51 | 0.48 |
| | 64 | 0.04 | 0.10 | 0.06 | 0.09 | 0.24 | 0.44 | 0.50 | 0.57 | 0.54 | 0.56 | 0.60 | 0.67 |
| | 32 | 0.04 | 0.04 | 0.16 | 0.23 | 0.35 | 0.43 | 0.46 | 0.53 | 0.53 | 0.57 | 0.62 | 0.72 |
| | 16 | 0.04 | 0.07 | 0.21 | 0.28 | 0.40 | 0.53 | 0.55 | 0.53 | 0.55 | 0.54 | 0.62 | 0.73 |
| | 8 | 0.05 | 0.04 | 0.28 | 0.27 | 0.44 | 0.49 | 0.52 | 0.55 | 0.54 | 0.54 | 0.63 | 0.69 |
| | 4 | 0.05 | 0.09 | 0.34 | 0.41 | 0.51 | 0.54 | 0.58 | 0.57 | 0.57 | 0.56 | 0.67 | 0.72 |
| | 0 | 0.05 | 0.50 | 0.42 | 0.57 | 0.62 | 0.70 | 0.66 | 0.76 | 0.71 | 0.76 | 0.73 | 0.72 |

Figure 42

| | | \multicolumn{11}{c|}{Colistin} |
|---|---|---|---|---|---|---|---|---|---|---|---|---|
| | | 64 | 32 | 16 | 8 | 4 | 2 | 1 | 0.5 | 0.25 | 0.125 | 0.0625 | 0 |
| HT0120365 | 256 | 0.05 | 0.05 | 0.05 | 0.05 | 0.57 | 0.64 | 0.66 | 0.72 | 0.72 | 0.66 | 0.71 | 0.62 |
| | 128 | 0.04 | 0.04 | 0.04 | 0.04 | 0.42 | 0.55 | 1.59 | 0.67 | 0.64 | 0.82 | 0.65 | 0.72 |
| | 64 | 0.04 | 0.04 | 0.04 | 0.04 | 0.45 | 0.50 | 0.54 | 0.61 | 0.80 | 0.80 | 0.64 | 0.82 |
| | 32 | 0.05 | 0.04 | 0.38 | 0.29 | 0.50 | 0.52 | 0.55 | 0.60 | 0.57 | 0.62 | 0.64 | 0.76 |
| | 16 | 0.04 | 0.04 | 0.16 | 0.44 | 0.50 | 0.58 | 0.56 | 0.56 | 0.58 | 0.58 | 0.68 | 0.78 |
| | 8 | 0.34 | 0.04 | 0.44 | 0.44 | 0.54 | 0.53 | 0.55 | 0.57 | 0.65 | 0.56 | 0.69 | 0.73 |
| | 4 | 0.05 | 0.04 | 0.31 | 0.46 | 0.55 | 0.57 | 0.58 | 0.61 | 0.63 | 0.60 | 0.71 | 0.73 |
| | 0 | 0.05 | 0.24 | 0.59 | 0.68 | 0.69 | 0.72 | 0.71 | 0.78 | 0.74 | 0.79 | 0.72 | 0.73 |

Figure 43

| | | \multicolumn{11}{c|}{Colistin} | | | | | | | | | | |
|---|---|---|---|---|---|---|---|---|---|---|---|---|
| | | 32 | 16 | 8 | 4 | 2 | 1 | 0.5 | 0.25 | 0.125 | 0.0625 | 0.03125 | 0 |
| HT0120417 | 256 | 0.04 | 0.04 | 0.04 | 0.05 | 0.05 | 0.20 | 0.32 | 0.42 | 0.47 | 0.48 | 0.49 | 0.50 |
| | 128 | 0.04 | 0.04 | 0.04 | 0.05 | 0.05 | 0.28 | 0.42 | 0.50 | 0.50 | 0.56 | 0.51 | 0.49 |
| | 64 | 0.05 | 0.04 | 0.04 | 0.05 | 0.05 | 0.34 | 0.51 | 0.53 | 0.54 | 0.60 | 0.54 | 0.54 |
| | 32 | 0.04 | 0.04 | 0.04 | 0.05 | 0.06 | 0.44 | 0.50 | 0.54 | 0.55 | 0.52 | 0.56 | 0.51 |
| | 16 | 0.04 | 0.04 | 0.05 | 0.06 | 0.27 | 0.47 | 0.51 | 0.54 | 0.53 | 0.56 | 0.57 | 0.51 |
| | 8 | 0.04 | 0.04 | 0.05 | 0.06 | 0.38 | 0.50 | 0.51 | 0.53 | 0.61 | 0.58 | 0.56 | 0.51 |
| | 4 | 0.04 | 0.04 | 0.05 | 0.12 | 0.44 | 0.51 | 0.54 | 0.56 | 0.57 | 0.57 | 0.57 | 0.53 |
| | 0 | 0.05 | 0.06 | 0.12 | 0.17 | 0.46 | 0.51 | 0.53 | 0.53 | 0.53 | 0.53 | 0.54 | 0.55 |

Figure 44

| | | \multicolumn{11}{c|}{HT0120707} | | | | | | | | | | |
|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.40 | 0.40 | 0.40 | 0.39 | 0.39 | 0.65 | 0.65 | 0.52 | 0.40 | 0.59 | 0.39 | 0.39 |
| | 16 | 0.41 | 0.39 | 0.40 | 0.41 | 0.40 | 0.40 | 0.40 | 0.39 | 0.40 | 0.40 | 0.40 | 0.40 |
| | 8 | 0.40 | 0.40 | 0.40 | 0.41 | 0.59 | 0.67 | 0.47 | 0.76 | 0.76 | 0.72 | 0.72 | 0.68 |
| | 4 | 0.39 | 0.39 | 0.40 | 0.45 | 0.53 | 0.58 | 0.60 | 0.67 | 0.69 | 0.65 | 0.77 | 0.80 |
| | 2 | 0.40 | 0.39 | 0.40 | 0.46 | 0.77 | 0.81 | 0.87 | 0.82 | 0.87 | 0.81 | 0.90 | 1.07 |
| | 1 | 0.40 | 0.40 | 0.40 | 0.78 | 0.91 | 0.93 | 0.93 | 0.95 | 0.85 | 0.89 | 0.86 | 1.13 |
| | 0.5 | 0.40 | 0.39 | 0.62 | 0.81 | 0.90 | 0.94 | 0.94 | 0.94 | 0.97 | 0.95 | 0.94 | 1.12 |
| | 0 | 0.40 | 0.62 | 0.70 | 1.05 | 1.10 | 1.13 | 1.12 | 1.12 | 1.13 | 1.15 | 1.14 | 1.18 |

Figure 45

| | | \multicolumn{11}{c|}{HT0120700} | | | | | | | | | | |
|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.40 | 0.40 | 0.40 | 0.40 | 0.40 | 0.40 | 0.40 | 0.40 | 0.40 | 0.40 | 0.40 | 0.40 |
| | 16 | 0.57 | 0.43 | 0.40 | 0.51 | 0.40 | 0.40 | 0.39 | 0.40 | 0.43 | 0.40 | 0.50 | 0.68 |
| | 8 | 0.40 | 0.40 | 0.40 | 0.49 | 0.40 | 0.46 | 0.46 | 0.60 | 0.67 | 0.63 | 0.62 | 0.83 |
| | 4 | 0.40 | 0.40 | 0.40 | 0.56 | 0.63 | 0.73 | 0.65 | 0.77 | 0.70 | 0.68 | 0.86 | 0.89 |
| | 2 | 0.40 | 0.39 | 0.40 | 0.58 | 0.79 | 0.83 | 0.85 | 0.86 | 0.83 | 0.88 | 0.94 | 1.09 |
| | 1 | 0.40 | 0.40 | 0.48 | 0.78 | 0.86 | 0.86 | 0.87 | 0.89 | 0.86 | 0.90 | 0.99 | 1.12 |
| | 0.5 | 0.40 | 0.39 | 0.58 | 0.83 | 0.90 | 0.93 | 0.94 | 0.94 | 0.95 | 0.96 | 0.97 | 1.14 |
| | 0 | 0.41 | 0.78 | 0.73 | 1.08 | 1.11 | 1.17 | 1.14 | 1.13 | 1.14 | 1.13 | 1.11 | 1.15 |

Figure 46

| | | \multicolumn{11}{c|}{HT0120093} | | | | | | | | | | |
|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.39 | 0.38 | 0.36 | 0.36 | 0.35 | 0.36 | 0.36 | 0.36 | 0.36 | 0.35 | 0.36 | 0.36 |
| | 16 | 0.39 | 0.38 | 0.37 | 0.36 | 0.36 | 0.36 | 0.36 | 0.36 | 0.53 | 0.36 | 0.46 | 0.53 |
| | 8 | 0.42 | 0.38 | 0.36 | 0.35 | 0.36 | 0.36 | 0.36 | 0.37 | 0.54 | 0.41 | 0.51 | 0.44 |
| | 4 | 0.42 | 0.36 | 0.37 | 0.36 | 0.36 | 0.36 | 0.36 | 0.49 | 0.68 | 0.56 | 0.78 | 0.87 |
| | 2 | 0.41 | 0.37 | 0.37 | 0.36 | 0.36 | 0.63 | 0.82 | 0.57 | 0.80 | 0.80 | 0.78 | 0.95 |
| | 1 | 0.37 | 0.37 | 0.36 | 0.37 | 0.55 | 0.63 | 0.74 | 0.92 | 0.86 | 0.84 | 0.83 | 1.02 |
| | 0.5 | 0.37 | 0.36 | 0.37 | 0.53 | 0.57 | 0.68 | 0.81 | 0.85 | 0.88 | 0.82 | 0.96 | 0.98 |
| | 0 | 0.61 | 0.44 | 0.38 | 0.60 | 0.60 | 0.70 | 0.94 | 0.93 | 0.95 | 1.03 | 0.97 | 1.03 |

Figure 47

|  |  | 256 | 128 | 64 | 32 | 16 | 8 | 4 | 2 | 1 | 0.5 | 0.25 | 0 |
|---|---|---|---|---|---|---|---|---|---|---|---|---|---|
|  | 16 | 0.43 | 0.41 | 0.41 | 0.39 | 0.40 | 0.40 | 0.40 | 0.41 | 0.93 | 0.90 | 0.88 | 0.83 |
|  | 8 | 0.45 | 0.42 | 0.41 | 0.40 | 0.40 | 0.40 | 0.41 | 0.87 | 0.96 | 1.03 | 1.11 | 0.98 |
|  | 4 | 0.43 | 0.42 | 0.41 | 0.40 | 0.41 | 0.60 | 0.79 | 0.93 | 0.98 | 1.10 | 1.15 | 1.04 |
| Colistin | 2 | 0.42 | 0.42 | 0.42 | 0.42 | 0.63 | 0.76 | 0.90 | 0.96 | 1.03 | 1.16 | 1.15 | 1.23 |
|  | 1 | 0.42 | 0.41 | 0.43 | 0.64 | 0.66 | 0.87 | 1.02 | 1.09 | 1.05 | 1.10 | 1.18 | 1.20 |
|  | 0.5 | 0.44 | 0.41 | 0.42 | 0.68 | 0.78 | 0.96 | 1.13 | 1.17 | 1.09 | 1.09 | 1.23 | 1.28 |
|  | 0.25 | 0.44 | 0.42 | 0.47 | 0.69 | 0.74 | 1.01 | 1.17 | 1.24 | 1.19 | 1.21 | 1.25 | 1.34 |
|  | 0 | 0.83 | 0.77 | 0.87 | 0.81 | 0.84 | 1.09 | 1.18 | 1.24 | 1.25 | 1.27 | 1.29 | 1.33 |

Figure 48

|  |  | 64 | 32 | 16 | 8 | 4 | 2 | 1 | 0.5 | 0.25 | 0.125 | 0.0625 | 0 |
|---|---|---|---|---|---|---|---|---|---|---|---|---|---|
|  | 256 | 0.05 | 0.04 | 0.04 | 0.04 | 0.05 | 0.05 | 0.05 | 0.20 | 0.27 | 0.47 | 0.51 | 0.53 |
|  | 128 | 0.05 | 0.04 | 0.06 | 0.07 | 0.04 | 0.04 | 0.08 | 0.31 | 0.33 | 0.37 | 0.39 | 0.50 |
|  | 64 | 0.04 | 0.05 | 0.09 | 0.06 | 0.10 | 0.06 | 0.36 | 0.47 | 0.42 | 0.44 | 0.45 | 0.51 |
| HT0120492 | 32 | 0.05 | 0.05 | 0.04 | 0.06 | 0.04 | 0.07 | 0.37 | 0.40 | 0.41 | 0.47 | 0.45 | 0.54 |
|  | 16 | 0.05 | 0.04 | 0.04 | 0.05 | 0.07 | 0.08 | 0.38 | 0.42 | 0.45 | 0.45 | 0.44 | 0.52 |
|  | 8 | 0.05 | 0.09 | 0.10 | 0.09 | 0.15 | 0.34 | 0.42 | 0.46 | 0.40 | 0.45 | 0.45 | 0.53 |
|  | 4 | 0.05 | 0.12 | 0.07 | 0.07 | 0.17 | 0.40 | 0.44 | 0.48 | 0.44 | 0.44 | 0.42 | 0.55 |
|  | 0 | 0.07 | 0.05 | 0.04 | 0.18 | 0.45 | 0.51 | 0.52 | 0.53 | 0.51 | 0.53 | 0.54 | 0.52 |

Figure 49

|  |  | 16 | 8 | 4 | 2 | 1 | 0.5 | 0.25 | 0.125 | 0.0625 | 0.03125 | 0.015625 | 0 |
|---|---|---|---|---|---|---|---|---|---|---|---|---|---|
|  | 256 | 0.05 | 0.04 | 0.04 | 0.04 | 0.04 | 0.13 | 0.34 | 0.44 | 0.51 | 0.58 | 0.58 | 0.72 |
|  | 128 | 0.05 | 0.04 | 0.05 | 0.04 | 0.04 | 0.07 | 0.32 | 0.43 | 0.46 | 0.45 | 0.55 | 0.63 |
|  | 64 | 0.04 | 0.04 | 0.06 | 0.04 | 0.04 | 0.06 | 0.36 | 0.44 | 0.48 | 0.54 | 0.54 | 0.60 |
| HT0120098 | 32 | 0.06 | 0.05 | 0.04 | 0.04 | 0.17 | 0.26 | 0.35 | 0.40 | 0.47 | 0.46 | 0.59 | 0.61 |
|  | 16 | 0.04 | 0.04 | 0.04 | 0.08 | 0.14 | 0.16 | 0.37 | 0.41 | 0.47 | 0.47 | 0.55 | 0.61 |
|  | 8 | 0.04 | 0.05 | 0.04 | 0.05 | 0.08 | 0.23 | 0.37 | 0.48 | 0.46 | 0.49 | 0.53 | 0.63 |
|  | 4 | 0.30 | 0.04 | 0.04 | 0.04 | 0.08 | 0.33 | 0.40 | 0.42 | 0.53 | 0.60 | 0.55 | 0.61 |
|  | 0 | 0.04 | 0.05 | 0.05 | 0.38 | 0.50 | 0.58 | 0.60 | 0.60 | 0.66 | 0.66 | 0.65 | 0.71 |

COMBINATION AND USE

CROSS REFERENCE TO RELATED APPLICATIONS

This application is a National Stage of International Application No. PCT/GB2015/054069 filed Dec. 18, 2015, claiming priorities based on British Patent Application Nos. 1422670.8, filed Dec. 18, 2014, 1500278.5, filed Jan. 8, 2015, and 1521901.7, filed Dec. 11, 2015, the contents of all of which are incorporated herein by reference in their entirety.

BACKGROUND OF THE INVENTION

The present invention relates to the use of certain known compounds in combination with an anti-microbial agent for the treatment of microbial infections. Additionally the present invention relates to the use of suloctidil or a pharmaceutically acceptable derivative or prodrug thereof in combination with polymyxin E or polymyxin B or a pharmaceutically acceptable derivative thereof for the treatment of microbial infections. In particular, it relates to the use of such combinations to kill multiplying and/or clinically latent microorganisms associated with microbial infections.

Before the introduction of antibiotics, patients suffering from acute microbial infections (e.g. tuberculosis or pneumonia) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (*Nature Reviews, Drug Discovery*, 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (*Lancet*, 357, 1179 (2001) and *Lancet*, 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics. Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, e.g. with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps. Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (*Science*, 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many microbial infections include sub-populations of bacteria that are phenotypically resistant to antimicrobials (*J. Antimicrob. Chemother.*, 4, 395-404 (1988); *J. Med. Microbiol.*, 38, 197-202 (1993); *J. Bacteriol.*, 182, 1794-1801 (2000); ibid. 182, 6358-6365 (2000); ibid. 183, 6746-6751 (2001); *FEMS Microbiol. Lett.*, 202, 59-65 (2001); and *Trends in Microbiology*, 13, 34-40 (2005)). There appear to be several types of such phenotypically resistant bacteria, including persisters, stationary-phase bacteria, as well as those in the depths of biofilms. However, each of these types is characterised by its low rate of growth compared to log-phase bacteria under the same conditions. Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (*Proc. Natl. Acad. Sci. USA*, 92, 11736-11740 (1995); *J. Bacteriol.*, 179, 6688-6691 (1997); and *Antimicrob. Agents Chemother.*, 44, 1771-1777 (2000)).

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

Recently, there has been report of an anti-retroviral drug, zidovudine being active as an anti-microbial when combined with gentamicin. Thus, Doléans-Jordheim A. et al., disclosed (Eur J Clin Microbiol Infect Dis. 2011 October; 30(10):1249-56) that Zidovudine (AZT) had a bactericidal effect on some enterobacteria, yet could induce resistance in *Escherichia coli*. These resistances were associated with various modifications in the thymidine kinase gene. Furthermore, an additive or synergistic activity between AZT and the two aminoglycoside antibiotics amikacin and gentamicin was observed against enterobacteria.

International Patent Application, Publication Number WO2012032360 discloses that certain classes of biologically active compounds possess bactericidal activity. One of these classes is vasodilators including compounds such as perhexiline maleate, suloctidil or nisoldipine.

International Patent Application published as WO2014/147405 describes the use of zidovudine in combination with a polymyxin selected from colistin and polymyxin B for treating a microbial infection.

Polymyxins are antibiotic compounds with a general structure consisting of a cyclic peptide and a long hydrophobic tail. They are known to disrupt the structure of the bacterial cell membrane by interacting with its phospholipids, and polymyxins B and E are typically used in the treatment of Gram-negative bacterial infections. Polymyxin E is otherwise known as "Colistin", and is commercially available in Europe under the trade name Colomycin® in tablet form. Colomycin® tablets include the sulphate salt of colistin and are indicated for the treatment of gastrointestinal infections caused by sensitive Gram negative organisms, as well as for bowel preparation. Polymyxin B is commercially available in Europe under the trade name Maxitrol® in the form of eye drops. Maxitrol® eye drops include polymyxin B in form of the sulphate salt, and are indicated for the short term treatment of steroid responsive conditions of the eye when prophylactic antibiotic treatment is also required, after excluding the presence of fungal and viral disease.

Given the importance of antimicrobial agents such as polymyxins in the fight against bacterial infection, the identification of further agents capable of enhancing their anti-bacterial activity addresses an important need.

BRIEF SUMMARY OF THE INVENTION

The present invention is thus based on the unexpected finding that the combinations and in particular the combination of suloctidil and colistin exhibit synergistic antimicrobial activity against log phase (i.e. multiplying) and/or clinically latent microorganisms, i.e. greater than the expected additive effect of each agent at the stated dosage level. The surprising biological activity of the combinations of the present invention offers the opportunity to shorten chemotherapy regimens and may result in a reduction in the emergence of microbial resistance associated with the use of such combinations.

Synergy in the context of antimicrobial drugs is measured in a number of ways that conform to the generally accepted opinion that "synergy is an effect greater than additive". One of the ways to assess whether synergy has been observed is to use the "chequerboard" technique. This is a well-accepted method that leads to the generation of a value called the fractional inhibitory concentration index (FICI). Orhan et al J. Clin. Microbiol. 2005, 43(1):140 describes the chequerboard method and analysis in the paragraph bridging pages 140-141, and explains that the FICI value is a ratio of the sum of the MIC (Minimum Inhibitory Concentration) level of each individual component alone and in the mixture. The combination is considered synergistic when the $\Sigma$FIC is <0.5, indifferent when the $\Sigma$FIC is >0.5 to <4.0, and antagonistic when the $\Sigma$FIC is >4.0.

Another accepted test for ascertaining the presence or absence of synergy is to use time-kill methods where the dynamic effect of a drug combination is compared to each drug alone when assessing the effect on bacterial log or stationary-growth over time. Again, the possible results are for synergistic, additive or antagonistic effects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figures 35, 36, 37, 38:
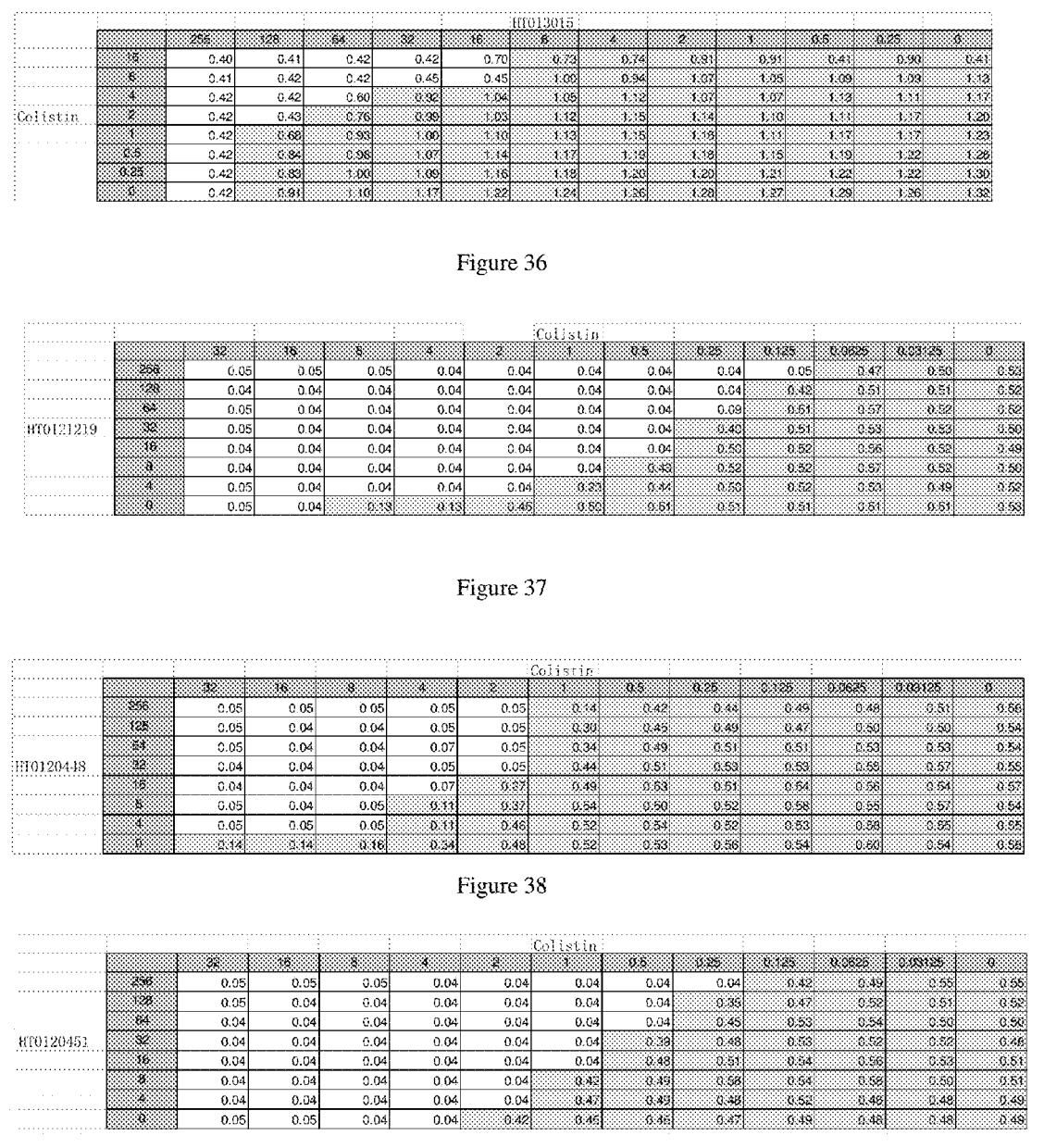

FIGS. 35-40 are each a chequerboard showing synergy between colistin and each of HT013015 (thymol), HT0121219 (aspirin), HT0120448 (ibuprofen), HT0120451 (indomethacin), HT0120566 (trifluoperazine hydrochloride), and HT0121567 (dichlorophen) against log phase NDM-1 *Klebsiella pneumonia*, respectively.

FIGS. 41-49 are each a chequerboard showing synergy between colistin and each of HT0120969 (benzydamine hydrochloride), HT0120365 (diclofenac sodium), HT0120417 (flurbiprofen), HT0120707 (chlorprothixene hydrochloride), HT0120700 (triflupromazine hydrochloride), HT0120093 (suloctidil), HT0120492 (piroxicam) and HT0120098 (saccharin) against log phase NDM-1 *E. coli*, respectively.

DETAILED DESCRIPTION OF THE INVENTION

Figure 1:
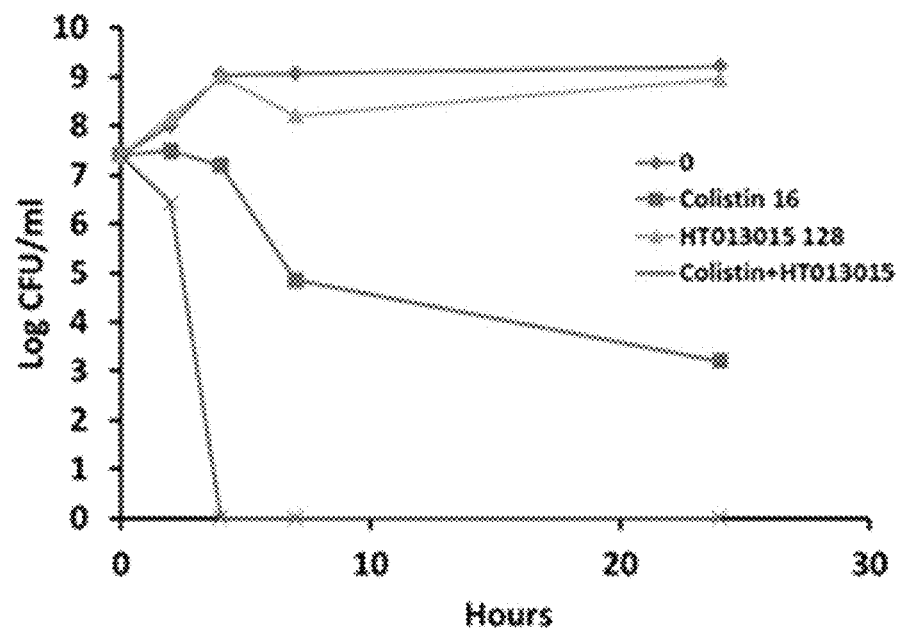
FIG. 1 is the time kill curve showing combination of colistin and HT013015 against NDM-1 *K. pneumoniae*.

Thus, in one embodiment, the present invention provides a combination comprising suloctidil or a pharmaceutically acceptable derivative or prodrug thereof, and a polymyxin selected from polymyxin E and polymyxin B or a pharmaceutically acceptable derivative thereof. Preferably the polymyxin is polymyxin E or a pharmaceutically acceptable derivative thereof.

Additionally there is provided a pharmaceutical composition comprising suloctidil or a pharmaceutically acceptable derivative or prodrug thereof in combination with a polymyxin selected from polymyxin E and polymyxin B or a pharmaceutically acceptable derivative thereof, and a pharmaceutically acceptable adjuvant, diluent or carrier. Preferably the pharmaceutical composition is for use in the treatment of a microbial infection.

In a further embodiment the present invention provides the use of suloctidil or a pharmaceutically acceptable derivative or prodrug thereof in combination with a polymyxin selected from polymyxin E and polymyxin B or a pharmaceutically acceptable derivative thereof, for the manufacture of a medicament for the prevention and/or treatment of a microbial infection.

In a further embodiment, the invention provides a method of preventing or treating a microbial infection which comprises administering to a mammal, including man, suloctidil or a pharmaceutically acceptable derivative or prodrug thereof in combination with a polymyxin selected from polymyxin E and polymyxin B or a pharmaceutically acceptable derivative thereof.

In another embodiment, the invention provides the use of suloctidil or a pharmaceutically acceptable derivative or prodrug thereof in combination with a polymyxin selected from polymyxin E and polymyxin B or a pharmaceutically acceptable derivative thereof for the prevention and/or treatment of a microbial infection.

Additionally the present invention provides the use of one or more compounds selected from the following: caffeic acid, thymol, aspirin, benzydamine hydrochloride, diclofenac sodium, flurbiprofen, ibuprofen, indomethacin, trifluoperazine hydrochloride, chlorprothixene hydrochloride, triflupromazine hydrochloride, suloctidil, thioridazine hydrochloride, dichlorophen, saccharin and piroxicam in combination with a polymyxin selected from colistin or polymyxin B or a pharmaceutically acceptable derivative thereof, for treating a microbial infection.

In a further embodiment, the invention provides a method of treating a microbial infection which comprises administering to a mammal, including man, one or more compounds selected from the following: caffeic acid, thymol, aspirin, benzydamine hydrochloride, diclofenac sodium, flurbiprofen, ibuprofen, indomethacin, trifluoperazine hydrochloride, chlorprothixene hydrochloride, triflupromazine hydrochloride suloctidil, thioridazine hydrochloride, dichlorophen, saccharin and piroxicam in combination with a polymyxin selected from colistin or polymyxin B or a pharmaceutically acceptable derivative thereof.

There is also provided a pharmaceutical composition comprising one or more compounds selected from the following: caffeic acid, thymol, aspirin, benzydamine hydrochloride, diclofenac sodium, flurbiprofen, ibuprofen, indomethacin, trifluoperazine hydrochloride, chlorprothixene hydrochloride, triflupromazine hydrochloride suloctidil, thioridazine hydrochloride, dichlorophen, saccharin and piroxicam, in combination with a polymyxin selected from colistin and polymyxin B or a pharmaceutically acceptable derivative thereof, and a pharmaceutically acceptable adjuvant, diluent or carrier, for use in the treatment of a microbial infection, preferably the microbial infection is a bacterial infection.

In a further embodiment, the invention relates to a product comprising one or more compounds selected from: caffeic acid (hydroxycinnamic acid), thymol, aspirin, benzydamine hydrochloride, diclofenac sodium, flurbiprofen, ibuprofen, indomethacin, trifluoperazine hydrochloride, chlorprothixene hydrochloride, triflupromazine hydrochloride suloctidil, thioridazine hydrochloride, dichlorophen, saccharin and piroxicam, in combination with a polymyxin selected from colistin and polymyxin B or a pharmaceutically acceptable derivative thereof, as a combined preparation for simultaneous, separate or sequential use in killing clinically latent microorganism associated with a microbial infection.

According to a further embodiment of the invention, there is provided a product comprising suloctidil or a pharmaceutically acceptable derivative or prodrug thereof, and a polymyxin selected from polymyxin E and polymyxin B or a pharmaceutically acceptable derivative thereof as a combined preparation for simultaneous, separate or sequential use in the prevention and/or treatment of a microbial infection.

The present invention therefore relates to:

the use of caffeic acid for the treatment of a microbial infection in combination with colistin;

the use of thymol for the treatment of a microbial infection in combination with colistin;

the use of aspirin for the treatment of a microbial infection in combination with colistin;

the use of benzydamine hydrochloride for the treatment of a microbial infection in combination with colistin;

the use of diclofenac sodium for the treatment of a microbial infection in combination with colistin;

the use of flurbiprofen for the treatment of a microbial infection in combination with colistin;

the use of ibuprofen for the treatment of a microbial infection in combination with colistin;

the use of indomethacin for the treatment of a microbial infection in combination with colistin;

the use of trifluoperazine hydrochloride for the treatment of a microbial infection in combination with colistin;

the use of chlorprothixene hydrochloride for the treatment of a microbial infection in combination with colistin;

the use of triflupromazine hydrochloride for the treatment of a microbial infection in combination with colistin;

the use of suloctidil or a pharmaceutically acceptable derivative or prodrug thereof for the treatment of a microbial infection in combination with colistin;

a combination comprising suloctidil or a pharmaceutically acceptable derivative or prodrug thereof and colistin or a pharmaceutically acceptable derivative thereof;

the use of thioridazine hydrochloride for the treatment of a microbial infection in combination with colistin;

the use of dichlorophen for the treatment of a microbial infection in combination with colistin;

the use of saccharin for the treatment of a microbial infection in combination with colistin; and the use of piroxicam for the treatment of a microbial infection in combination with colistin.

Colistin can also be included in the above combinations in the form of a pharmaceutically acceptable derivative as defined herein, e.g. as a salt such as colistin sulphate.

As described below, the combinations of the present invention have been demonstrated to be particularly effective against drug-resistant bacteria, particularly Gram-negative bacteria, opening the way for said combinations to be administered both to drug-resistant strains and in said strains before drug-resistance is built up, i.e. as a first line treatment.

As used herein, the term "in combination with" covers both separate and sequential administration of the compound and the polymyxin. When the compound and polymyxin are administered sequentially, either the compound or the polymyxin may be administered first. When administration is simultaneous, the compound and polymyxin may be administered either in the same or a different pharmaceutical composition. Adjunctive therapy, i.e. where one agent is used as a primary treatment and the other agent is used to assist that primary treatment, is also an embodiment of the present invention.

The combinations of the present invention may be used to treat microbial infections. In particular they may be used to kill multiplying and/or clinically latent microorganisms associated with microbial infections. References herein to the treatment of a microbial infection therefore include killing multiplying and/or clinically latent microorganisms associated with such infections. Preferably, the combinations of the present invention are used to kill clinically latent microorganisms associated with microbial infections.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or (II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

In one embodiment of the invention, one or more of the aforementioned combinations is used to treat a bacterial infection in particular, the combinations may be used to kill clinically latent microorganisms associated with a bacterial infection. As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*);

Streptococci (e.g.beta-haemolytic, pyogenic streptococci (such as *Strept. agalactiae, Strept. canis, Strept. dysgalactiae dysgalactiae, Strept. dysgalactiae equisimilis, Strept. equi equi, Strept. equi zooepidemicus, Strept. iniae, Strept. porcinus* and *Strept. pyogenes*), microaerophilic, pyogenic streptococci (*Streptococcus* "milleri", such as *Strept. anginosus, Strept. constellatus constellatus, Strept. constellatus pharyngidis* and *Strept. intermedius*), oral streptococci of the "*mitis*" (alpha-haemolytic—*Streptococcus* "*viridans*", such as *Strept. mitis, Strept. oralis, Strept. sanguinis, Strept. cristatus, Strept. gordonii* and *Strept. parasanguinis*), "*salivarius*" (non-haemolytic, such as *Strept. salivarius* and *Strept. vestibularis*) and "*mutans*" (tooth-surface streptococci, such as *Strept. criceti, Strept. mutans, Strept. ratti* and *Strept. sobrinus*) groups, *Strept. acidominimus, Strept. bovis, Strept. faecalis, Strept. equinus, Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri*;

Bacillaceae, such as *Bacillus anthracis, Bacillus subtilis, Bacillus thuringiensis, Bacillus stearothermophilus* and *Bacillus cereus*;

Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*);

Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);

*Helicobacter* (e.g. *Helicobacter pylori, Helicobacter cinaedi* and *Helicobacter fennelliae*); *Acinetobacter* (e.g. *A. baumanii, A. calcoaceticus, A. haemolyticus, A. johnsonii, A. junii, A. lwoffi* and *A. radioresistens*);

*Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzen*);

*Bacteroides fragilis*;

*Peptococcus* (e.g. *Peptococcus niger*);

*Peptostreptococcus*;

*Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonnii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*);

*Mycoplasma* (e.g. *M. pneumoniae, M. hominis, M. genitalium* and *M. urealyticum*); Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*);

*Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*);

*Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*);

*Actinomyces* (e.g. *Actinomyces israelii*);

*Brucella* (e.g. *Brucella abortus, Brucella canis, Brucella melintensis* and *Brucella suis*);

*Campylobacter* (e.g. *Campylobacter jejuni, Campylobacter coli, Campylobacter lari* and *Campylobacter fetus*);

*Listeria monocytogenes*;

*Vibrio* (e.g. *Vibrio cholerae* and *Vibrio parahaemolyticus, Vibrio alginolyticus, Vibrio carchariae, Vibrio fluvialis, Vibrio fumissii, Vibrio hollisae, Vibrio metschnikovii, Vibrio mimicus* and *Vibrio vulnificus*);

*Erysipelothrix rhusopathiae*;

Corynebacteriaceae (e.g. *Corynebacterium diphtheriae, Corynebacterium jeikeum* and *Corynebacterium urealyticum*);

Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*);

*Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*);

*Bordetella* (e.g. *Bordetella bronchiseptica, Bordetella hinzii, Bordetella holmseii, Bordetella parapertussis, Bordetella pertussis* and *Bordetella trematum*);

Nocardiaceae, such as *Nocardia* (e.g. *Nocardia asteroides* and *Nocardia brasiliensis*);

*Rickettsia* (e.g. *Ricksettsii* or *Coxiella burnetii*);

*Legionella* (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachernii, Legionalla micdadei, Legionalla oakridgensis, Legionalla pneumophila, Legionalla sainthelensi, Legionalla tucsonensis* and *Legionalla wadsworthii*);

*Moraxella catarrhalis*;

*Cyclospora cayetanensis*;

*Entamoeba histolytica;*
*Giardia lamblia;*
*Trichomonas vaginalis;*
*Toxoplasma gondii;*
*Stenotrophomonas maltophilia;*
*Burkholderia cepacia; Burkholderia mallei* and *Burkholderia pseudomallei;*
*Francisella tularensis;*
*Gardnerella* (e.g. *Gardneralla vaginalis* and *Gardneralla mobiluncus*);
*Streptobacillus moniliformis;*
Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);
*Bartonella* (*Bartonella bacilliformis, Bartonella clarridgeiae, Bartonella elizabethae, Bartonella henselae, Bartonella quintana* and *Bartonella vinsonii arupensis*);
*Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);
*Spirillium* (e.g. *Spirillum minus*);
Baceteroides (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);
*Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis* and *Prevotella zoogleoformans*);
*Porphyromonas* (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*);
*Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);
*Chlamydia* (e.g. *Chlamydia trachomatis*);
*Cryptosporidium* (e.g. *C. parvum, C. hominis, C. canis, C. fells, C. meleagridis* and *C. muris*);
*Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*));
*Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);
*Gemella* (e.g. *Gemella bergeri, Gemella haemolysans, Gemella morbillorum* and *Gemella sanguinis*); and
*Ureaplasma* (e.g. *Ureaplasma parvum* and *Ureaplasma urealyticum*).

Preferably, the bacterial infections treated by the combinations described herein are gram-negative infections.

Particular bacteria that may be treated using a combination of the invention include Gram negative bacteria: Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*);
*Haemophilis influenzae;*
Mycobacteria, such as *Mycobacterium tuberculosis.*

Preferably, the bacterium is Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*). The combination of the present invention is particularly beneficial in treating (multi)-drug-resistant ((M)DR) bacteria. With respect to Enterobacteriaceae, drug resistance most often builds up to carbapenemase i.e. carbapenemase-resistant strains and "extended spectrum β-lactamase" (ESBL) strains for example New Delhi Metallo-beta-lactamase-1 (NDM-1) resistant *Klebs. Pneumonia*.

More preferably the bacterium is *Escherichia coli* or *Klebsiella* (e.g. Klebs. *pneumoniae*).

It should be kept in mind that although a combination such as that claimed may initially be demonstrated to be functional in treating (M)DR strains, they can then be used in treating non-resistant strains. This is especially valuable in the context of the presently claimed combination where the primary therapy for Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*) are anti-microbial drugs that are expensive due to prevailing patent protection. The replacement of such "ethical" drugs by a combination of "generic" antibiotics is thought to be beneficial from a therapeutic perspective as well as financial/economic perspective in times where governments are seeking to reduce the cost of healthcare.

The combinations of the present invention may be used to treat infections associated with any of the above-mentioned bacterial organisms, and in particular they may be used for killing multiplying and/or clinically latent microorganisms associated with such an infection.

Particular conditions which may be treated using the combination of the present invention include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, asthma, bacillary dysentery, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, nephritis, diffuse panbronchiolitis, diphtheria, dental caries, diseases of the upper respiratory tract, eczema, empyema, endocarditis, endometritis, enteric fever, enteritis, epididymitis, epiglottitis, erysipelas, erysipelas, erysipeloid, erythrasma, eye infections, furuncles, gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, ricin poisoning, Ritter's disease, salmonellosis, salpingitis, septic arthritis, septic infections, septicameia, sinusitis, skin infections (e.g. skin granulomas, impetigo, folliculitis and furunculosis), syphilis, systemic infections, tonsillitis, toxic shock syndrome, trachoma, tularaemia, typhoid, typhus (e.g. epidemic typhus, murine typhus, scrub typhus and spotted fever), urethritis, urinary tract infections, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilis influenzae, Enterococcus faecalis* and *Enterococcus faecium*. In particular, the combination in kidney stone associated infections and catheter-associated infections arising from any of the bacteria described.

It will be appreciated that references herein to "treatment" extend to prophylaxis as well as the treatment of established diseases or symptoms.

As used herein the term "pharmaceutically acceptable derivative" means:
(a) pharmaceutically acceptable salts; and/or
(b) solvates (including hydrates).

Pharmaceutically acceptable salts and solvates (including hydrates) are also understood to include polymorphs such as pseudopolymorphs, packing polymorphs and conformational polymorphs.

A review of suitable pharmaceutical salts may be found in Berge et al, J Pharm Sci, 66, 1-19 (1977) as well as P. H. Stahl and C. G. Wermuth, editors, *Handbook of Pharmaceutical Salts: Properties, Selection and Use*, Weinheim/Zürich: Wiley-VCH/VHCA, 2002. Suitable acid addition salts include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

The antibacterial agent is preferably a polymyxin such as colistin and/or polymyxin B or a pharmaceutically acceptable derivative thereof. Particularly preferred is colistin or a pharmaceutically acceptable derivative thereof. A preferred salt of colistin is the sulfate salt thereof, i.e. polymyxin B sulfate. A preferred salt of polymyxin E is the sulfate salt thereof, i.e. polymyxin E sulfate.

Several of the compounds included in the combinations of the present invention including suloctidil, polymyxin B, colistin sulfate, polymyxin E sulfate and colistin are commercially available, for example from Sigma Aldrich Limited. Others may be prepared using conventional methods known in the art.

The invention further includes suloctidil in prodrug form, i.e. in the form of a covalently bonded compound which releases the active suloctidil in vivo. Suloctidil has the following formula:

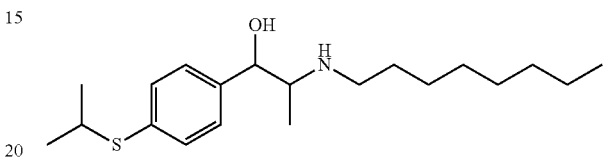

Such prodrugs are generally the active ingredient, i.e. suloctidil, wherein one or more appropriate groups (typically the OH or NH group) have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications to suloctidil include 1-N-substituted (acyloxy)-alkyl carbamate compounds and esters. With an ester prodrug the reversion to suloctidil may be carried out by an esterase.

Esters are typically formed using organic acids. Organic acids that may be used include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. In some cases it may be desirable to prepare double ester type prodrugs such as (acyloxy)alkyl esters or ((alkoxycarbonyl)oxy)alkyl esters).

In one embodiment the prodrug of suloctidil is a compound of formula (1):

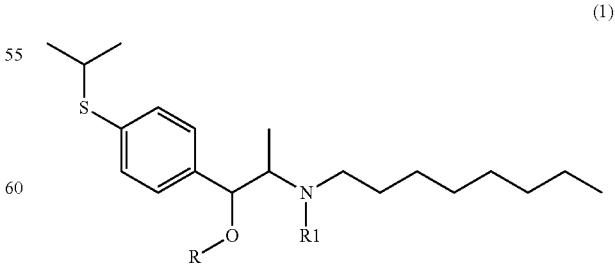

(1)

wherein:
R is H or $COR^a$ where $R^a$ is hydrogen, an optionally substituted alkyl group, an optionally substituted alkenyl group, an optionally substituted alkynyl group, an optionally substituted aryl group, an optionally substituted heteroaryl group, an optionally substituted carbocyclyl group, an optionally substituted heterocyclyl group, or an alkoxy group.

Representative COR$^a$ groups include, but are not limited to, formyl (—CHO), acetyl, (—C(O)CH$_3$), cyclohexylcarbonyl, cyclohexylmethylcarbonyl, benzoyl (C(O)Ph), benzylcarbonyl (C(O)CH$_2$Ph), C(O)—C$_{1-8}$alkyl, C(O)(CH$_2$)$_t$ (C$_6$-C$_{10}$aryl), C(O)(CH$_2$)$_t$(5-10 membered heteroaryl), C(O)(CH$_2$)$_t$(C$_3$-C$_{10}$cycloalkyl), and C(O)(CH$_2$)$_t$(4-10 membered heterocyclyl), wherein t is an integer from 0 to 4.

R$^a$ is preferably selected from C$_1$-C$_8$ alkyl or C$_1$-C$_4$ alkyl, each optionally substituted with halo, OH, OR$^b$, or NHSO$_2$R$^b$ wherein R$^b$ is C$_{1-4}$ alkyl; or C$_3$-C$_{10}$cycloalkyl, 4-10 membered heterocyclyl, C$_6$-C$_{10}$aryl, arylalkyl, 5-10 membered heteroaryl or heteroarylalkyl, each optionally substituted with C$_{1-4}$ alkyl, C$_{1-4}$ hydroxyalkyl, C$_{1-4}$ haloalkoxy, OH, OR$^b$, or NHSO$_2$R$^b$ wherein R$^b$ is C$_{1-4}$ alkyl. and wherein:

R$^1$ is H, or COCR$^c$R$^d$OC(O)R$^e$, wherein R$^c$ is H or an optionally substituted alkyl group, an optionally substituted alkenyl group, an optionally substituted alkynyl group, or an alkoxy group.

R$^c$ is preferably H or a group selected from C$_1$-C$_8$ alkyl or C$_1$-C$_4$ alkyl, each optionally substituted with halo, OH, OR$^b$, or NHSO$_2$R$^b$ wherein R$^b$ is C$_{1-4}$ alkyl, C$_3$-C$_{10}$cycloalkyl, 4-10 membered heterocyclyl, C$_6$-C$_{10}$aryl, 5-10 membered heteroaryl, wherein the C$_3$-C$_{10}$cycloalkyl, 4-10 membered heterocyclyl, C$_6$-C$_{10}$aryl, and 5-10 membered heteroaryl are each optionally substituted with C$_{1-4}$ alkyl, C$_{1-4}$ hydroxyalkyl, C$_{1-4}$ haloalkoxy, OH, OR$^b$, or NHSO$_2$R$^b$ wherein R$^b$ is C$_{1-4}$ alkyl.

More preferably R$^c$ is H or a group selected from C$_1$-C$_8$ alkyl or C$_1$-C$_4$ alkyl, each optionally substituted with halo, OH, OR$^b$, or NHSO$_2$R$^b$ wherein R$^b$ is C$_{1-4}$ alkyl. Most preferably R$^c$ is H or an unsubstituted C$_{1-4}$ alkyl.

R$^d$ is an optionally substituted alkyl group, an optionally substituted alkenyl group, an optionally substituted alkynyl group, or an alkoxy group.

R$^d$ is preferably a group selected from C$_1$-C$_8$ alkyl or C$_1$-C$_4$ alkyl, each optionally substituted with halo, OH, OR$^b$, or NHSO$_2$R$^b$ wherein R$^b$ is C$_{1-4}$ alkyl, C$_3$-C$_{10}$cycloalkyl, 4-10 membered heterocyclyl, C$_6$-C$_{10}$aryl, 5-10 membered heteroaryl, wherein the C$_3$-C$_{10}$cycloalkyl, 4-10 membered heterocyclyl, C$_6$-C$_{10}$aryl, and 5-10 membered heteroaryl are each optionally substituted with C$_{1-4}$ alkyl, C$_{1-4}$ hydroxyalkyl, C$_{1-4}$ haloalkoxy, OH, OR$^b$, or NHSO$_2$R$^b$ wherein R$^b$ is C$_{1-4}$ alkyl.

More preferably R$^d$ is selected from C$_1$-C$_8$ alkyl or C$_1$-C$_4$ alkyl, each optionally substituted with halo, OH, OR$^b$, or NHSO$_2$R$^b$ wherein R$^b$ is C$_{1-4}$ alkyl.

R$^e$ is an optionally substituted alkyl group, an optionally substituted alkenyl group, an optionally substituted alkynyl group, an optionally substituted aryl group, an optionally substituted heteroaryl group, an optionally substituted carbocyclyl group, an optionally substituted heterocyclyl group, or an alkoxy group.

Representative COR$^e$ groups include, but are not limited to, formyl (—CHO), acetyl, (—C(O)CH$_3$), cyclohexylcarbonyl, cyclohexylmethylcarbonyl, benzoyl (C(O)Ph), benzylcarbonyl (C(O)CH$_2$Ph), C(O)—C$_{1-8}$alkyl, C(O)(CH$_2$)$_t$ (C$_6$-C$_{10}$aryl), C(O)(CH$_2$)$_t$(5-10 membered heteroaryl), C(O)(CH$_2$)$_t$(C$_3$-C$_{10}$cycloalkyl), and C(O)(CH$_2$)$_t$(4-10 membered heterocycyl), wherein t is an integer from 0 to 4.

Preferably R$^e$ is a group selected from C$_1$-C$_8$ alkyl or C$_1$-C$_4$ alkyl, each optionally substituted with halo, OH, OR$^b$, or NHSO$_2$R$^b$ wherein R$^b$ is C$_{1-4}$ alkyl, C$_3$-C$_{10}$cycloalkyl, 4-10 membered heterocyclyl, C$_6$-C$_{10}$aryl, 5-10 membered heteroaryl, wherein the C$_3$-C$_{10}$cycloalkyl, 4-10 membered heterocyclyl, C$_6$-C$_{10}$aryl, and 5-10 membered heteroaryl are each optionally substituted with C$_{1-4}$ alkyl, C$_{1-4}$ hydroxyalkyl, C$_{1-4}$ haloalkoxy, OH, OR$^b$, or NHSO$_2$R$^b$ wherein R$^b$ is C$_{1-4}$ alkyl; or C$_3$-C$_{10}$cycloalkyl, 4-10 membered heterocyclyl, C$_6$-C$_{10}$aryl, arylalkyl, 5-10 membered heteroaryl or heteroarylalkyl, each optionally substituted with C$_{1-4}$ alkyl, C$_{1-4}$ hydroxyalkyl, C$_{1-4}$ haloalkoxy, OH, OR$^b$, or NHSO$_2$R$^b$ wherein R$^b$ is C$_{1-4}$ alkyl.

More preferably R$^d$ and R$^e$ are independently an unsubstituted C$_{1-4}$ alkyl group.

Provided that if R is H, R$^1$ is not H, and when R$^1$ is H, R is not H.

Alternatively R$^1$ is a group of formula (2) linked via the bond indicated, wherein R$^f$ is an optionally substituted C$_{1-4}$ alkyl group, aryl or alkoxyaryl. Preferably R$^f$ is an unsubstituted C$_{1-4}$ alkyl, phenyl or methoxyphenyl.

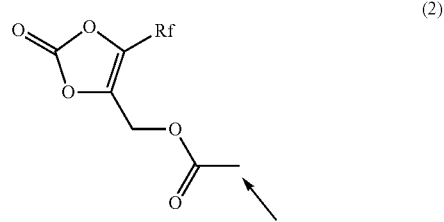

(2)

Compounds of formula (1) and (2) can be prepared by known methods by those skilled in the art. Suitable methods are disclosed in for example WO 2014/134005, or J. Med. Chem 1996, 39, 480. These methods are incorporated herein by reference.

Other prodrug systems will be well known to those skilled in the art.

As used herein, the term "alkyl" includes both saturated straight chain and branched alkyl groups which may be substituted (mono- or poly-) or unsubstituted. Preferably, the alkyl group is a C$_{1-15}$ alkyl group, more preferably a C$_{1-10}$ alkyl group, more preferably still a C$_{1-8}$ alkyl group, more preferably still a C$_{1-6}$ alkyl group. Particularly preferred alkyl groups include, for example, methyl, ethyl, n-propyl, iso-propyl, n-butyl, sec-butyl, tert-butyl, n-pentyl, tert-pentyl, neo-pentyl, iso-pentyl, sec-pentyl and 4-pentyl. In certain embodiments the alkyl group is substituted with halo, OH, OR$^b$, NHSO$_2$R$^b$ wherein R$^b$ is C$_{1-4}$ alkyl.

The term "halo" refers to fluoro, chloro, bromo or iodo.

As used herein, the term "aryl" refers to a C$_{6-18}$ aromatic group which may be substituted (mono- or poly-) or unsubstituted. Preferably the aryl group is a C$_{6-14}$ aryl group, more preferably a C$_{6-10}$ aryl group. Typical examples include phenyl, naphthyl, mesityl, benzyl, and anthracenyl, and a particularly preferred aryl group is phenyl, mesityl or benzyl, e.g. phenyl.

As used herein, the term "alkenyl" refers to a carbon chain containing one or more carbon-carbon double bonds, which may be branched or unbranched, and substituted (mono- or poly-) or unsubstituted. Preferably the alkenyl group is a C$_{2-20}$ alkenyl group, more preferably a C$_{2-15}$ alkenyl group, more preferably still a C$_{2-10}$ alkenyl group, more preferably still a C$_{2-8}$ alkenyl group, or more preferably still a C$_{2-6}$ alkenyl group.

As used herein, the term "alkynyl" refers to a carbon chain containing one or more carbon-carbon triple bonds, which may be branched or unbranched, and substituted (mono- or poly-) or unsubstituted. Preferably the alkynyl group is a $C_{2-20}$ alkynyl group, more preferably a $C_{2-15}$ alkynyl group, more preferably still a $C_{2-10}$ alkynyl group, more preferably still a $C_{2-5}$ alkynyl group, or more preferably still a $C_{2-6}$ alkynyl group.

As used herein, the term "cycloalkyl" refers to a mono- or multi-ringed cyclic alkyl group which may be substituted (mono- or poly-) or unsubstituted. Preferably the cycloalkyl is a mono-ringed group. Preferably a $C_3$-$C_7$ cycloalkyl group, particularly preferred are cyclopentane, cyclohexane and cycloheptane groups, e.g. cyclopentane or cyclohexane. In another embodiment, the cycloalkyl is a multi-ringed group, e.g. adamantyl.

As used herein, the term "heterocyclyl" refers to heteroaryl, heterocycloalkyl and heterocycloalkenyl groups. The term "heteroaryl" refers to an aryl group as defined above wherein at least one ring atom is a heteroatom. Suitable heteroatoms will be apparent to those skilled in the art and include, for example, sulphur, nitrogen, oxygen, phosphorus and silicon. Particularly preferred is when the heteroatom is sulphur, nitrogen or oxygen.

Monocyclic heteroaryl groups include for example, furan, pyrrole, thiophene, imidazole, oxazole, thiazole, 1,3,4-thiadiazole, isothiazole, isoxazole, oxadiazole, oxazole, 1,2,3-oxadiazole, pyrazole, triazole, tetrazole, pyridine, pyrazine, pyrimidine, pyridazines, triazine and tetrazine. Bicyclic or polycyclic heteroaryl groups may include a monocyclic heteroaryl group as defined herein, fused to one or more groups independently selected from an aryl group, a cycloalkyl group, a cycloalkenyl group and another monocyclic heteroaryl group. For example, the heteroaryl group may be indole, benzimidazole, benzothiazole, benzofuran, indoline, quinolone, isoquinoline, isoindole, indazole, phenylpiperidine or benzothiene.

The terms "heterocycloalkyl" and "heterocycloalkenyl" respectively refer to a cycloalkyl group or a cycloalkenyl group as defined above, wherein at least one ring atom in the cycloalkyl or cycloalkenyl group is a heteroatom. Again, suitable heteroatoms will be apparent to those skilled in the art and include, for example, sulphur, nitrogen, oxygen, phosphorus and silicon. Particularly preferred is when the heteroatom is sulphur, nitrogen or oxygen, e.g. aziridine, tetrahydrofuran, pyrrolidine, pyrroline, piperidine, piperazine, thiazolidine, oxazolidine, morpholine, thiane, thiazine, pyrazolidine, pyrazoline, imidazolidine or imidazoline.

The term "alkoxy" refers to an O-alkyl group, wherein alkyl is as defined above. Preferably, the alkoxy group is a $C_{1-20}$ alkoxy group, more preferably a $C_{1-15}$ alkoxy group, more preferably still a $C_{1-10}$ alkoxy group, more preferably still a $C_{1-8}$ alkoxy group, more preferably still a $C_{1-6}$ alkoxy group. Particularly preferred alkoxy groups include, for example, methoxy, ethoxy, iso-propoxy, propoxy, butoxy, iso-butoxy, pentoxy and hexyloxy.

Further preferred antimicrobial compounds for use in the present invention are those capable of killing clinically latent microorganisms. Methods for determining activity against clinically latent bacteria include a determination, under conditions known to those skilled in the art (such as those described in *Nature Reviews, Drug Discovery*, 1, 895-910 (2002), the disclosures of which are hereby incorporated by reference), of Minimum Stationary-cidal Concentration ("MSC") or Minimum Dormicidal Concentration ("MDC") for a test compound. A suitable compound screening method against clinically latent microorganisms is described in WO2000028074, the contents of which are incorporated herein by reference as if the publication was specifically and fully set forth herein.

Compounds for use according to the invention may be administered as the raw material but the active ingredients are preferably provided in the form of pharmaceutical compositions.

The active ingredients may be used either as separate formulations or as a single combined formulation. When combined in the same formulation it will be appreciated that the two compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient. Preferably, the compositions of the invention are formulated for oral or topical administration. In a preferred embodiment, the composition is a cream or an ointment adapted for nasal administration, in particular for delivery to the anterior nares.

The formulations may conveniently be presented in unit dosage form and may be prepared by any of the methods well known in the art of pharmacy e.g. as described in "*Remington: The Science and Practice of Pharmacy*", Lippincott Williams and Wilkins, $21^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations.

Formulations suitable for oral administration may be presented as discrete units such as capsules, cachets or tablets (e.g. chewable tablets in particular for pediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described above, (e.g. any of the *Staphylococci*, *Streptococci*, *Mycobacteria* or *Pseudomonas* organisms mentioned hereinbefore, such as *S. aureus* (e.g. Methicillin resistant *S. aureus* (MRSA))).

Particular bacterial conditions that may be treated by topical pharmaceutical compositions of the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii*, *M. malmoense*, *M. szulgai*, *M. simiae*, *M. gordonae*, *M. haemophilum*, *M. avium*, *M. intracellulare*, *M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczema, burns, abrasions and skin wounds.

Compositions for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

Suitable dosages and formulations for the administration of colistin are described in the product label for Colomycin® which can be found at http://www.medicines.org.uk/emc/medicine/6301/SPC/Colomycin+Tablets/dosages and formulations for the administration of caffeic acid (hydroxycinnamic acid), thymol, aspirin, benzydamine hydrochloride, diclofenac sodium, flurbiprofen, ibuprofen, indomethacin, trifluoperazine hydrochloride, chlorprothixene hydrochloride, triflupromazine hydrochloride, suloctidil, thioridazine hydrochloride, dichlorophen, saccharin and piroxicam may be obtained from conventional sources such as www.medicine.org.uk, http://www.accessdata.fda.gov/scripts/cder/drugsatfda/index.cfm, www.rxlist.com and/or www.drugs.com. These sources disclose the therapeutic, safe doses for each of these drugs. When used in combination in accordance with the present invention, the dosage of said drug may be decreased from that known.

The administration of the combination of the invention by means of a single patient pack, or patients packs of each composition, including a package insert directing the patient to the correct use of the invention is a desirable feature of this invention.

According to a further embodiment of the present invention there is provided a patient pack comprising at least one active ingredient of the combination according to the invention and an information insert containing directions on the use of the combination of the invention.

In another embodiment of the invention, there is provided a double pack comprising in association for separate administration, an antimicrobial agent, preferably having biological activity against clinically latent microorganisms, and one or more of the compounds disclosed herein preferably having biological activity against clinically latent microorganisms.

According to a further embodiment of the present invention there is provided a patient pack comprising at least one active ingredient of the combinations according to the invention, i.e. at least one of suloctidil or a pharmaceutically acceptable derivative or prodrug thereof and a polymyxin selected from polymyxin E and polymyxin B or a pharmaceutically acceptable derivative thereof, and an information insert containing directions on the use of the combination.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-doses per day.

Biological Tests

Test procedures that may be employed to determine the biological (e.g. bactericidal or antimicrobial) activity of the active ingredients include those known to persons skilled in the art for determining:
  (a) bactericidal activity against clinically latent bacteria; and
  (b) antimicrobial activity against log phase bacteria.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:
  (1) growing a bacterial culture to stationery phase;
  (2) treating the stationery phase culture with one or more antimicrobial agents at a concentration and or time sufficient to kill growing bacteria, thereby selecting a phenotypically resistant sub-population;
  (3) incubating a sample of the phenotypically resistant subpopulation with one or more test compounds or agents; and
  (4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO 2005014585, the disclosures of which document are hereby incorporated by reference), of Minimum Inhibitory Concentration ("MIC") or Minimum Bactericidal Concentration ("MBC") for a test compound. Specific examples of such methods are described below.

EXAMPLES

The chequerboard method and Time kill experiments are described below and in Antimicrob Chemo (2013) 68, 374-384.

Example 1: Time Kill Experiments (a) Thymol (HT013015) and Colistin Against NDM-1 *Klebsiella pneumoniae*

FIG. 1 is the time kill curve showing combination of colistin and HT013015 against NDM-1 *K. pneumoniae.*

(b): Trifluoperazine Hydrochloride (HT0120566) and Colistin Against NDM-1 *Klebsiella pneumoniae*

Figure 2:
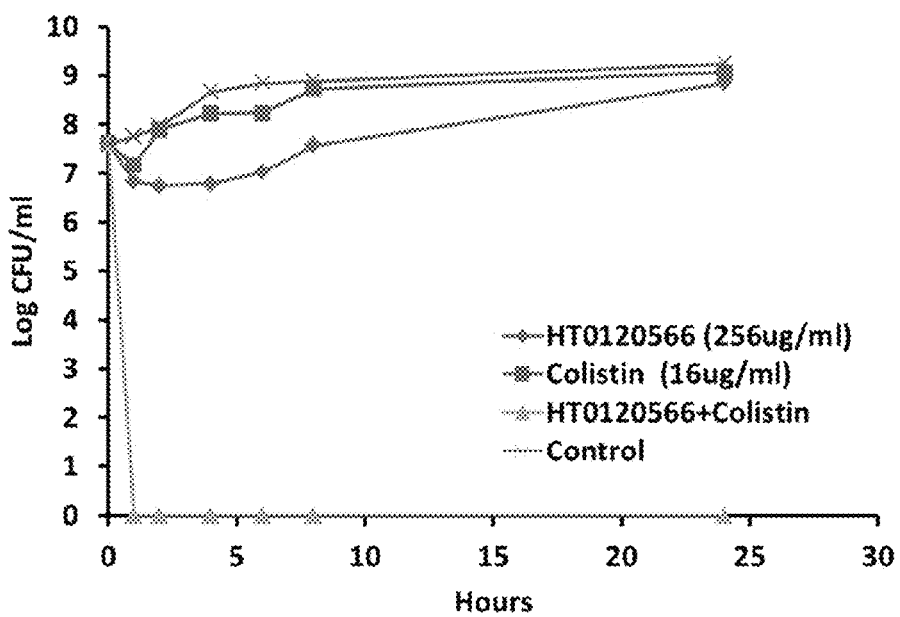
FIG. 2 is the time kill curve showing combination of colistin and HT0120566 against NDM-1 *Klebsiella pneumoniae*.

FIG. 2 is the time kill curve showing combination of colistin and HT0120566 against NDM-1 *Klebsiella pneumoniae.*

(c): Chlorprothixene Hydrochloride (HT0120707) and Colistin Against NDM-1 *E. coli*

Figure 3:
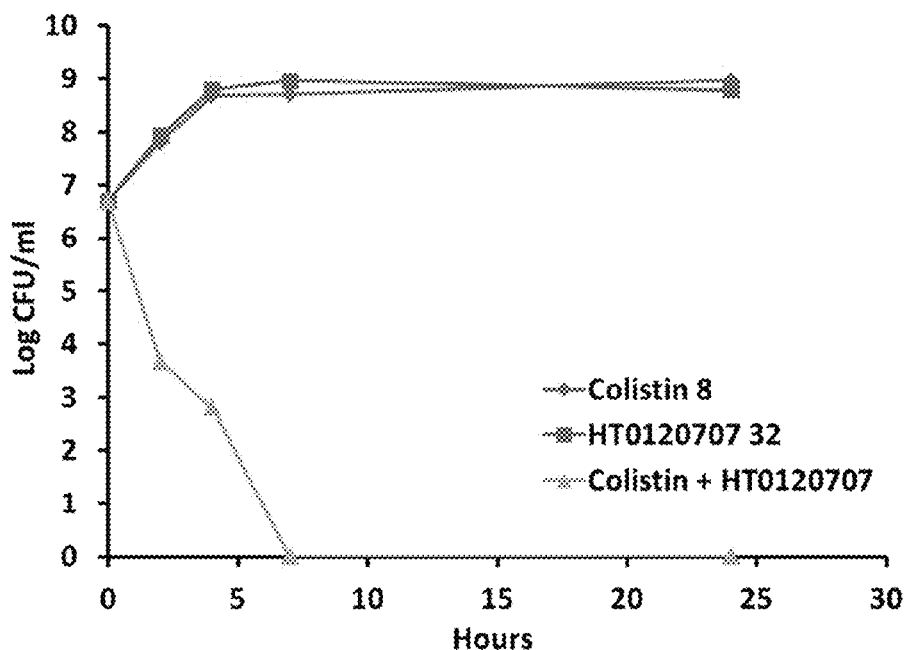
FIG. 3 is the time kill curve showing combination of colistin and HT0120707 against NDM-1 *E. coli*.

FIG. 3 is the time kill curve showing combination of colistin and HT0120707 against NDM-1 *E. coli.*

(d): Triflupromazine Hydrochloride (HT0120700) and Colistin Against NDM-1 *E. coli*

Figure 4:
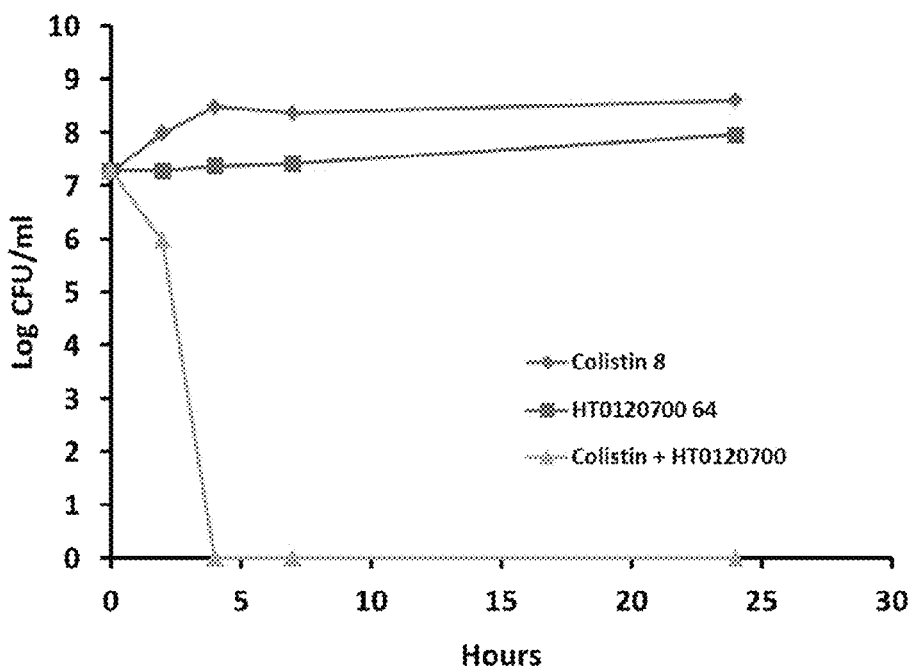
FIG. 4 is the time kill curve showing combination of colistin and HT0120700 against NDM-1 *E. coli*.

FIG. 4 is the time kill curve showing combination of colistin and HT0120700 against NDM-1 *E. coli.*

(e): Suloctidil (HT0120093) and Colistin Against NDM-1 *E. coli*

Figure 5:
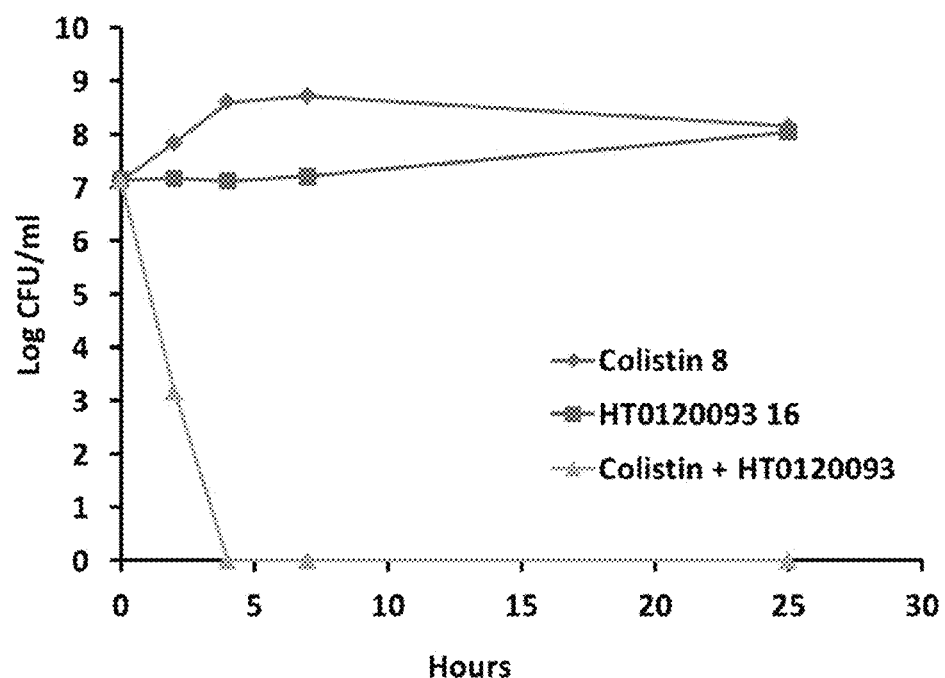
FIG. 5 is the time kill curve showing combination of colistin and HT0120093 against NDM-1 *E. coli*.

FIG. 5 is the time kill curve showing combination of colistin and HT0120093 against NDM-1 *E. coli.*

(f): Thioridazine Hydrochloride (HT0120553) and Colistin Against NDM-1 *Klebsiella pneumoniae*

Figure 6:
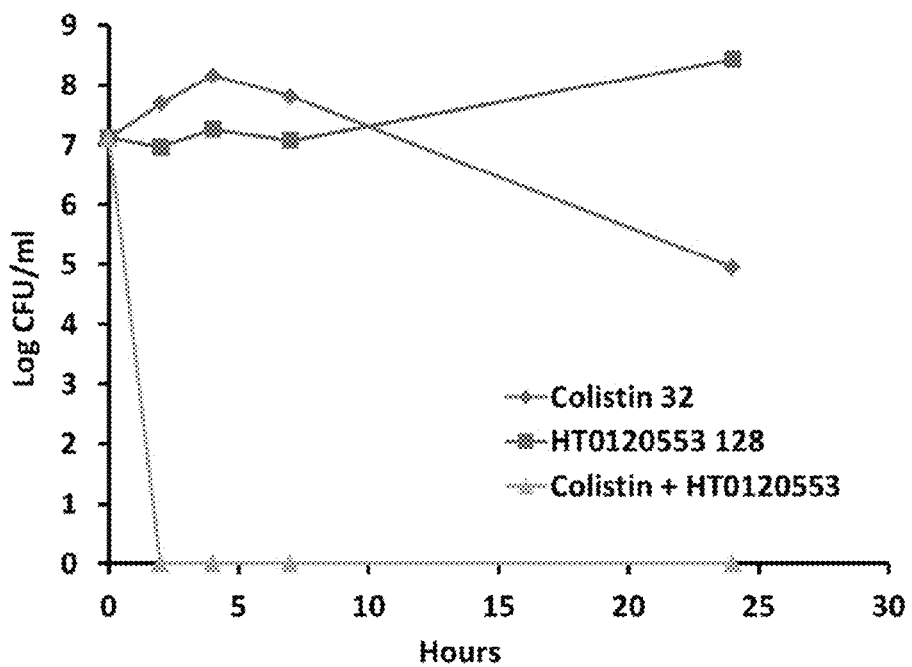
FIG. 6 is the time kill curve showing combination of colistin and HT0120553 against NDM-1 *Klebsiella pneumoniae*.

FIG. 6 is the time kill curve showing combination of colistin and HT0120553 against NDM-1 *Klebsiella pneumoniae.*

(g): Dichlorophen (HT0121567) and Colistin Against NDM-1 *K. pneumoniae*

Figure 7:
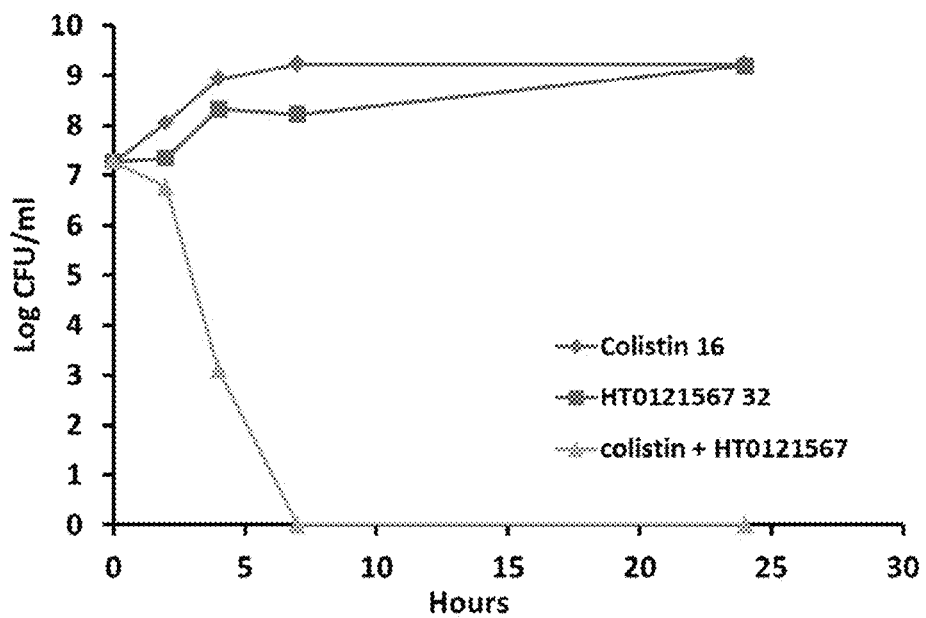
FIG. 7 is the time kill curve showing combination of colistin and HT0121567 against NDM-1 *K. pneumoniae*.

FIG. 7 is the time kill curve showing combination of colistin and HT0121567 against NDM-1 *K. pneumoniae.*

(h): Aspirin (HT0121219) and Colistin Against NDM-1 *Klebsiella pneumoniae*

Figure 8:
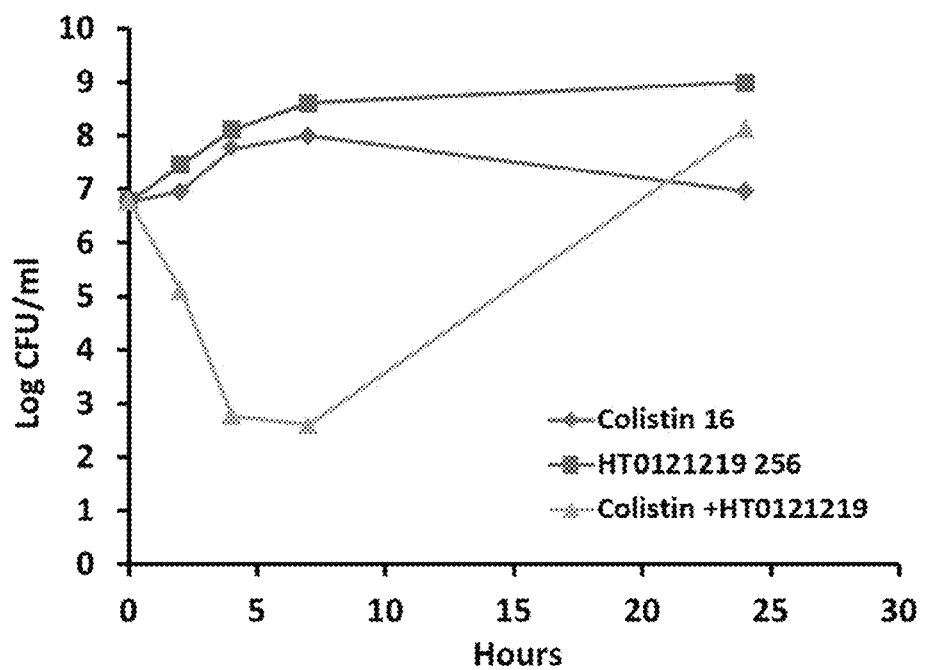
FIG. 8 is the time kill curve showing combination of colistin and HT0121219 against NDM-1 *K. pneumoniae*

FIG. 8 is the time kill curve showing combination of colistin and HT0121219 against NDM-1 *K. pneumoniae*

(i): Indomethacin (HT0120451) and Colistin Against NDM-1 *K. pneumoniae*

Figure 9:
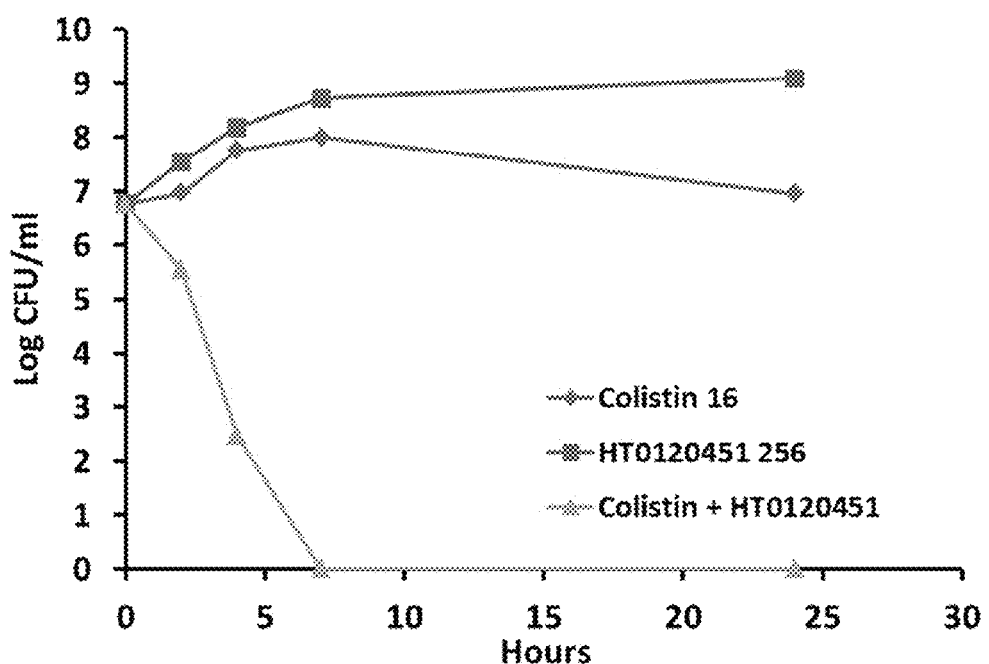
FIGS. 9 and 10 are the time kill curves showing combination of colistin and HT0120451 against NDM-1 *K. pneumoniae*.
Figure 10:
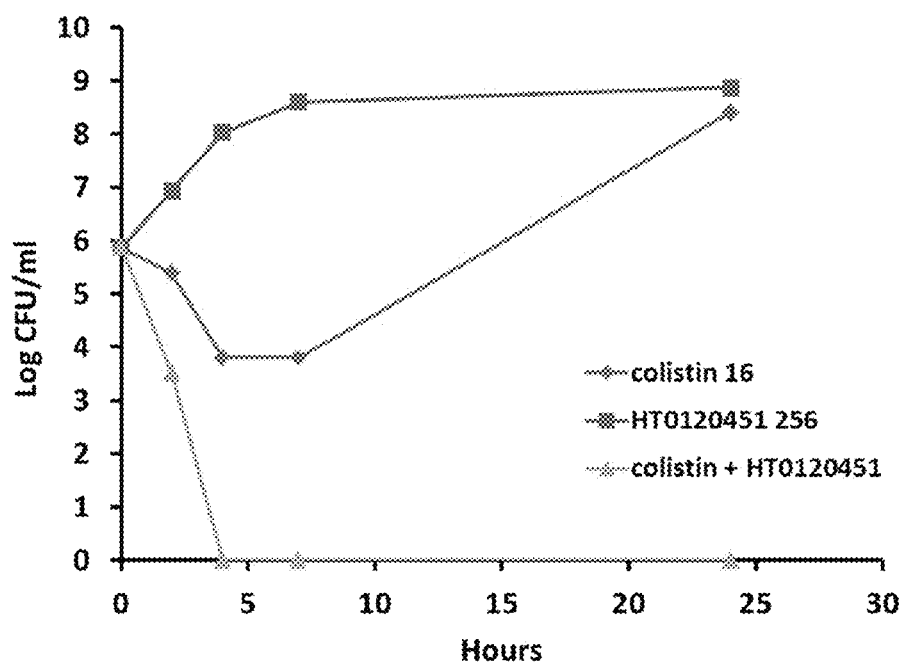

FIGS. 9 and 10 are the time kill curves showing combination of colistin and HT0120451 against NDM-1 *K. pneumoniae.*

(j): Piroxicam (HT0120492) and Colistin Against NDM-1 *E. coli*

Figure 11:
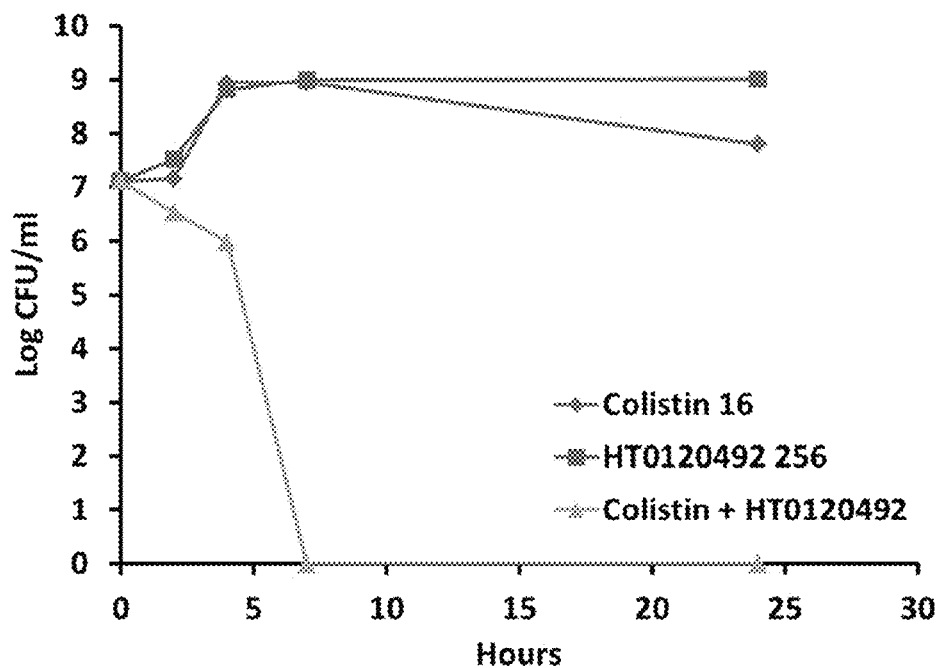
FIG. 11 is the time kill curve showing combination of colistin and HT0120492 against NDM-1 *E. coli*.

FIG. 11 is the time kill curve showing combination of colistin and HT0120492 against NDM-1 *E. coli.*

(k): Benzydamine Hydrochloride (HT0120969) and Colistin Against NDM-1 *E. coli*

Figure 12:
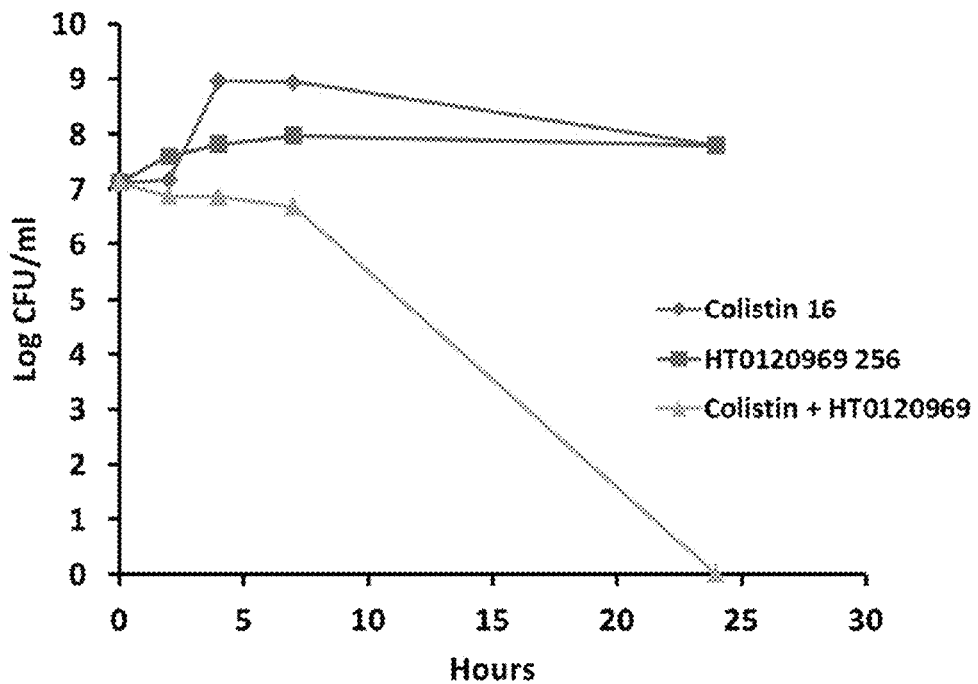
FIG. 12 is the time kill curve showing combination of colistin and HT0120969 against NDM-1 *E. coli*.

FIG. 12 is the time kill curve showing combination of colistin and HT0120969 against NDM-1 *E. coli.*

(l): Ibuprofen (HT0120448) and Colistin Against NDM-1 *K. pneumoniae*

Figure 13:
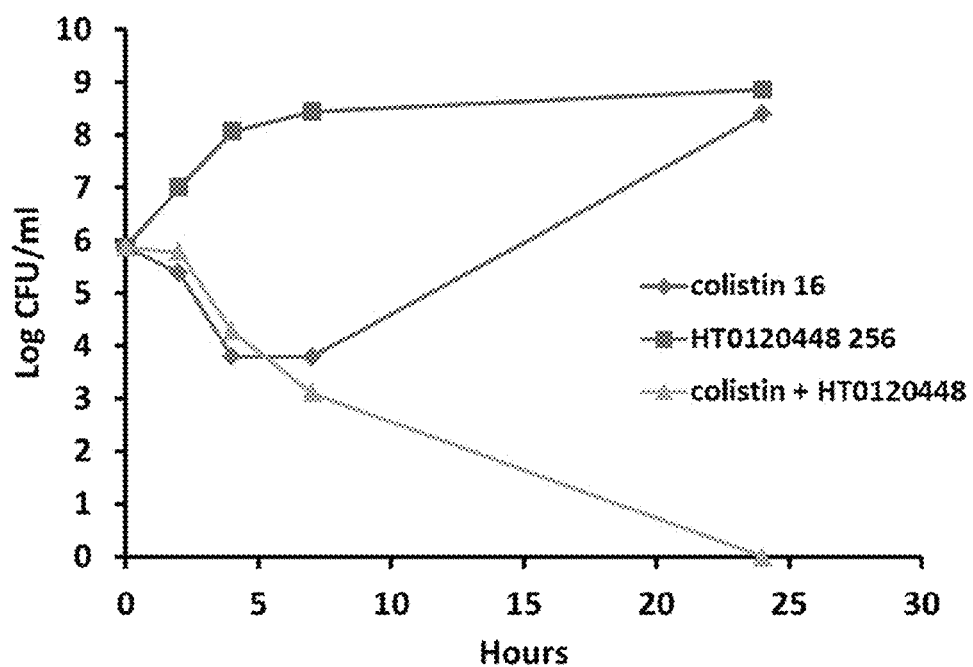
FIG. 13 is the time kill curve showing combination of colistin and HT0120448 against NDM-1 *Klebsiella pneumoniae*.

FIG. 13 is the time kill curve showing combination of colistin and HT0120448 against NDM-1 *Klebsiella pneumoniae.*

(m): Diclofenac Sodium (HT0120365) and Colistin Against NDM-1 *E. coli*

Figure 14:
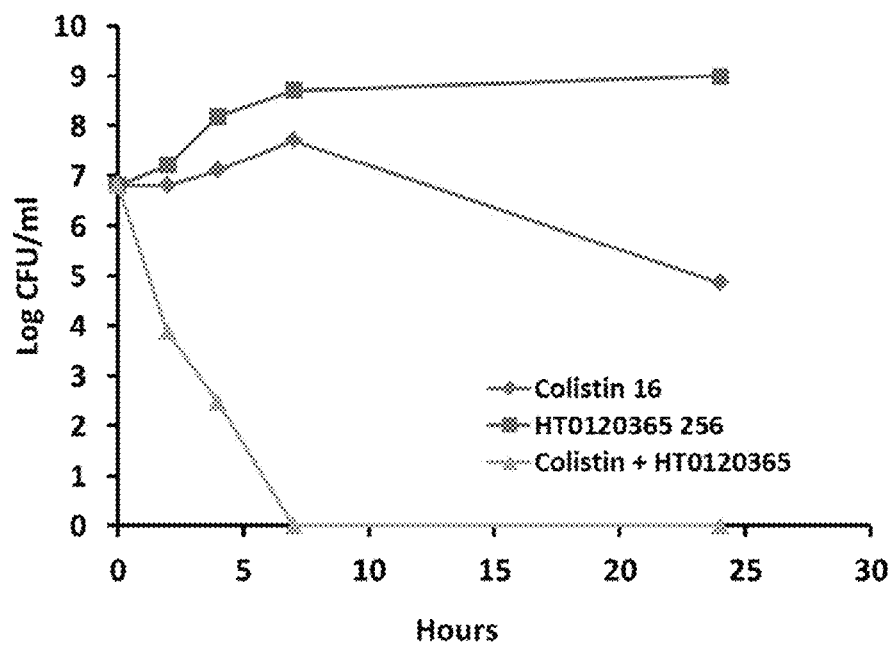
FIG. 14 is the time kill curve showing combination of colistin and HT0120365 against NDM-1 *E. coli*.

FIG. 14 is the time kill curve showing combination of colistin and HT0120365 against NDM-1 *E. coli*.

(n): Flurbiprofen (HT0120417) and Colistin Against NDM-1 *E. coli*

Figure 15:
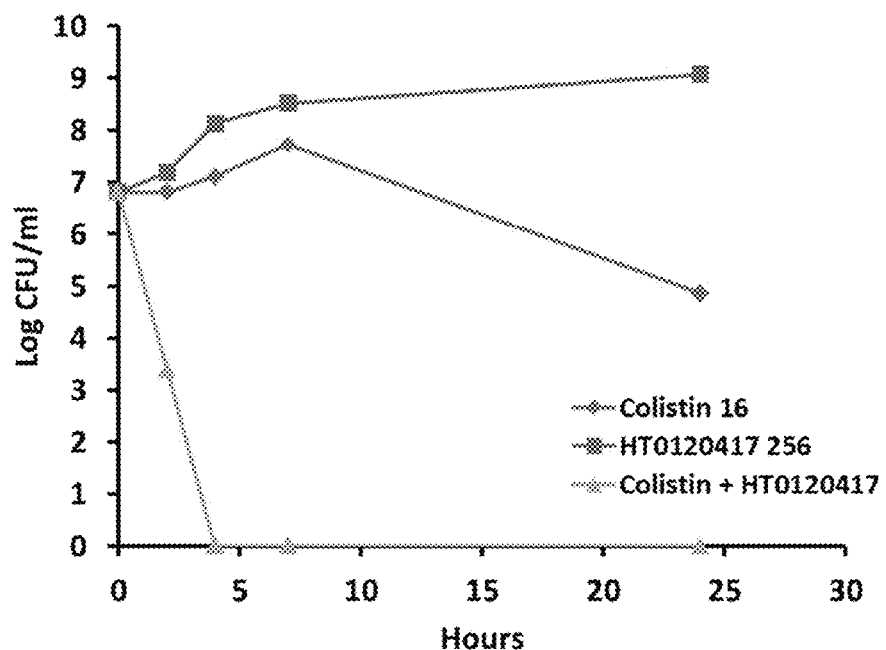
FIG. 15 is the time kill curve showing combination of colistin and HT0120417 against NDM-1 *E. coli*

FIG. 15 is the time kill curve showing combination of colistin and HT0120417 against NDM-1 *E. coli*

(o): Caffeic Acid (HT013001) and Colistin Against NDM-1 *E. coli*

Figure 16:
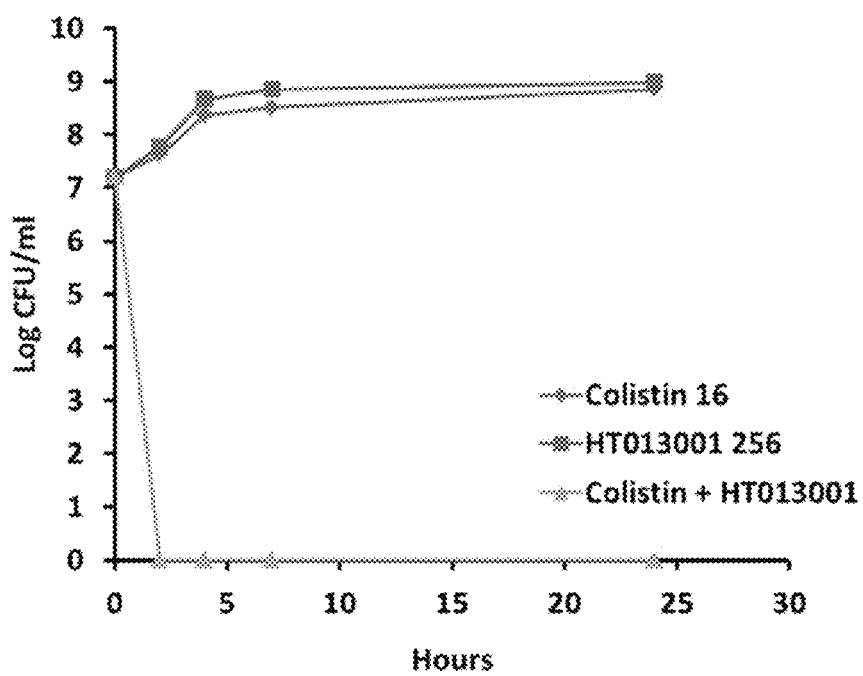
FIG. 16 is the time kill curve showing combination of colistin and HT013001 against NDM-1 *E. coli*

FIG. 16 is the time kill curve showing combination of colistin and HT013001 against NDM-1 *E. coli*

(p): Saccharin (HT0120098) and Colistin Against NDM-1 *E. coli*

Figure 17:
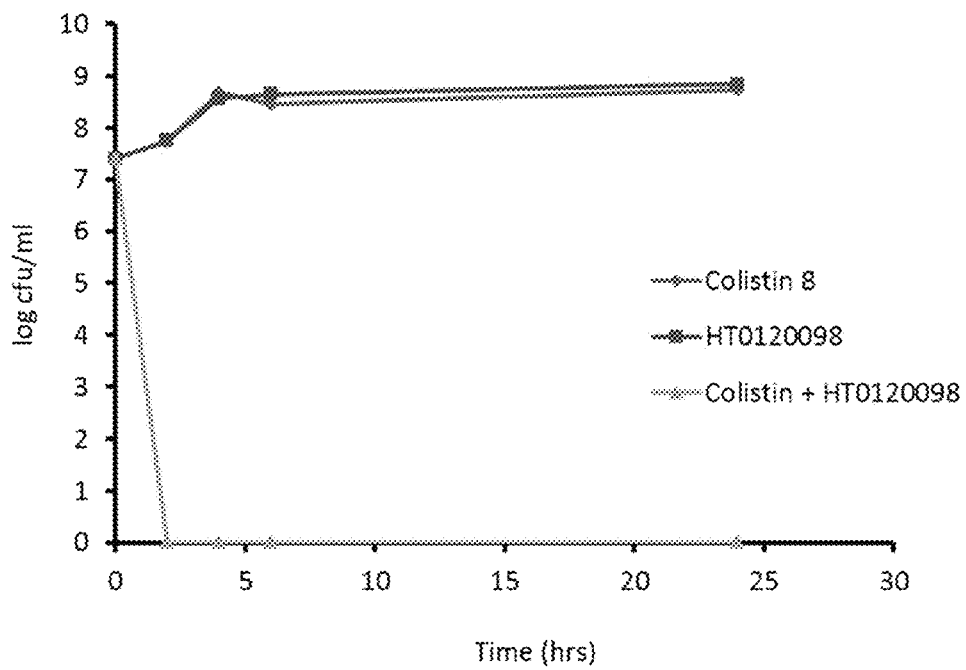
FIG. 17 is the time kill curve showing combination of colistin and HT0120098 against NDM-1 *E. coli*.
Figure 18:
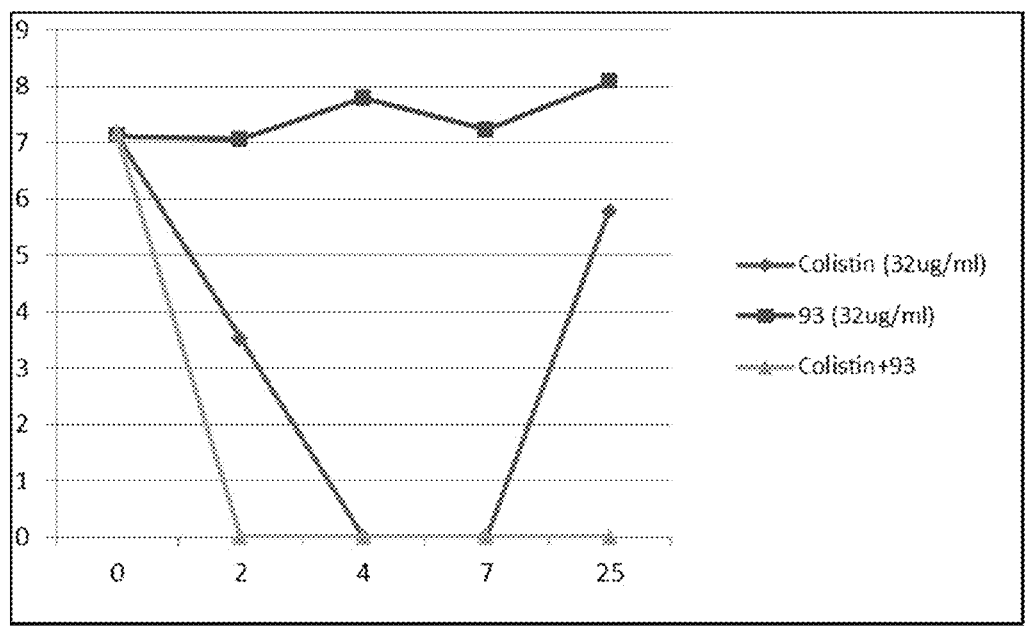
FIGS. 18-27 are time kill curves showing the combinations listed in Table 1. Suloctidil is referenced as "93".

FIG. 17 is the time kill curve showing combination of colistin and HT0120098 against NDM-1 *E. coli*.

Example 2: Chequerboard Method (a) In Vitro Synergy Effect of Colistin and Each of HT013015 (Thymol), HT0121219 (Aspirin), HT0120448 (Ibuprofen), HT0120451 (Indomethacin), HT0120566 (Trifluoperazine Hydrochloride), and HT0121567 (Dichlorophen) Against Log Phase NDM-1 *Klebsiella pneumoniae* Using the Chequerboard Method Growth of Bacteria Log phase growth of NDM-1 *Klebsiella pneumonia* was carried out as described in the art.

The effects of each combination of the present invention were examined by calculating the fractional inhibitory concentration index (FICI) of each combination, as follows: (MIC of drug A, tested in combination)/(MIC of drug A, tested alone)+(MIC of drug B, tested in combination)/(MIC of drug B, tested alone). The interaction of the combination was defined as showing synergy if the FICI was ≤0.5, no interaction if the FICI was >0.5 but <4.0 and antagonism if the FICI was >4.0. The results are depicted in FIGS. 35-40.

(b) In vitro synergy effect of colistin and each of HT0120969 (benzydamine hydrochloride), HT0120365 (diclofenac sodium), HT0120417 (flurbiprofen), HT0120707 (chlorprothixene hydrochloride), HT0120700 (triflupromazine hydrochloride), HT0120093 (suloctidil), HT0120492 (piroxicam) and HT0120098 (saccharin) against log phase NDM-1 *E. coli* using the chequerboard method Growth of Bacteria Log phase growth of NDM-1 *E. coli* was carried out as described in the art.

The effects of each combination of the present invention were examined by calculating the fractional inhibitory concentration index (FICI) of each combination, as follows: (MIC of drug A, tested in combination)/(MIC of drug A, tested alone)+(MIC of drug B, tested in combination)/(MIC of drug B, tested alone).

The interaction of the combination was defined as showing synergy if the FICI was ≤50.5, no interaction if the FICI was >0.5 but <4.0 and antagonism if the FICI was >4.0. The results are depicted in FIGS. 41-49.

Example 3

In Vitro Synergy Effect of Suloctidil in Combination with Colistin Against Log Phase NDM-1 *Klebsiella pneumoniae*

The synergistic effect of suloctidil in combination with colistin was tested against log phase NDM-1 *Klebsiella pneumoniae* using time-kill methods over a period of 24 hours.

Materials and Methods

Bacterial strain used: NCTC 13443 strain of NDM-1 *Klebsiella pneumoniae*

Growth of bacteria: Log phase growth of the bacteria was carried out according to methods known in the art.

Compounds and Preparation:

(i) Suloctidil was obtained from a commercial source and dissolved in DMSO to make a stock concentration of 10 mg/ml.

(ii) Colistin was obtained from a commercial source at a concentration of 20 mg/ml.

Both suloctidil and colistin were then added to 96 well plates either alone or in the combinations shown below in Table 1.

TABLE 1

| Agent (Concentration) | Number/Letter | Combination | Combination |
|---|---|---|---|
| Colistin (32 µg/ml) | 1 | 1&A | 1&C |
| Colistin (16 µg/ml) | 2 | 2&A | 2&C |
| Colistin (8 µg/ml) | 3 | 3&A | 3&C |
| Colistin (4 µg/ml) | 4 | 4&A | 4&C |
| Suloctidil (32 µg/ml) | A | 1&B | 1&D |
| Suloctidil (16 µg/ml) | B | 2&B | 2&D |
| Suloctidil (8 µg/ml) | C | 3&B | 3&D |
| Suloctidil (4 µg/ml) | D | 4&B | 4&D |

The overnight culture was diluted with nutrient broth (Oxoid) to $10^7$ CFU/ml and 280 µl and 290 µl of the culture was added to each combination well and single agent well, respectively, to make a final concentration of 300 µl. Incubation of the compounds with the bacterial suspension was carried out for 24 hours. At 0, 2, 4, 7 and 25 hours, CFU counts were performed to measure the kill effects of the drug combination.

Results

The time-kill curves are shown in FIGS. 18 to 27, where suloctidil is referenced as "93".

Summary and Conclusion

Figure 19:
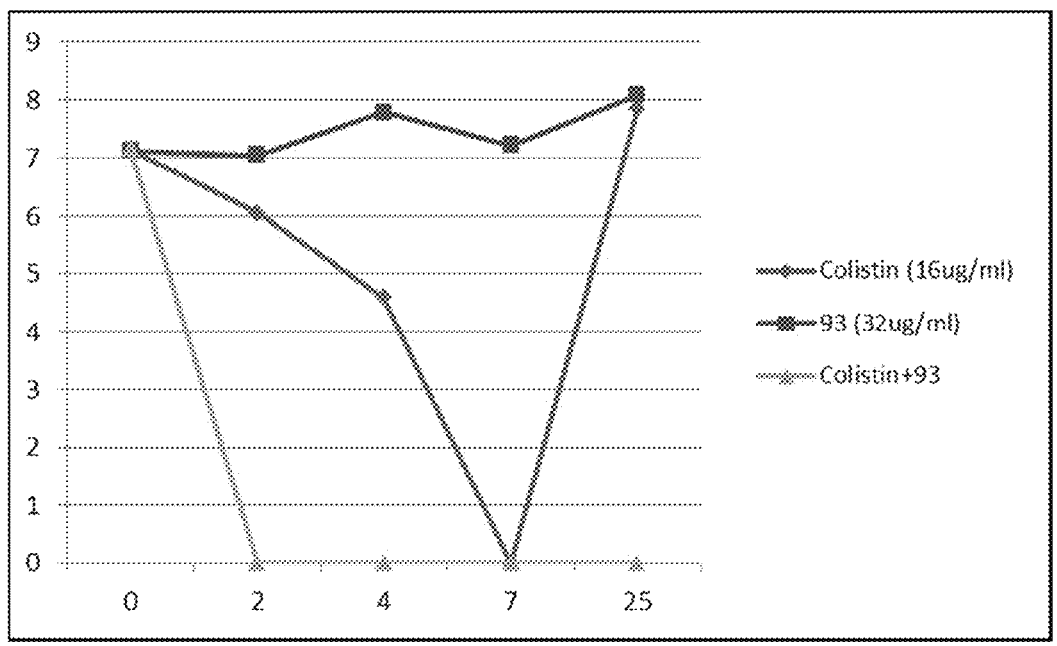
Figure 20:
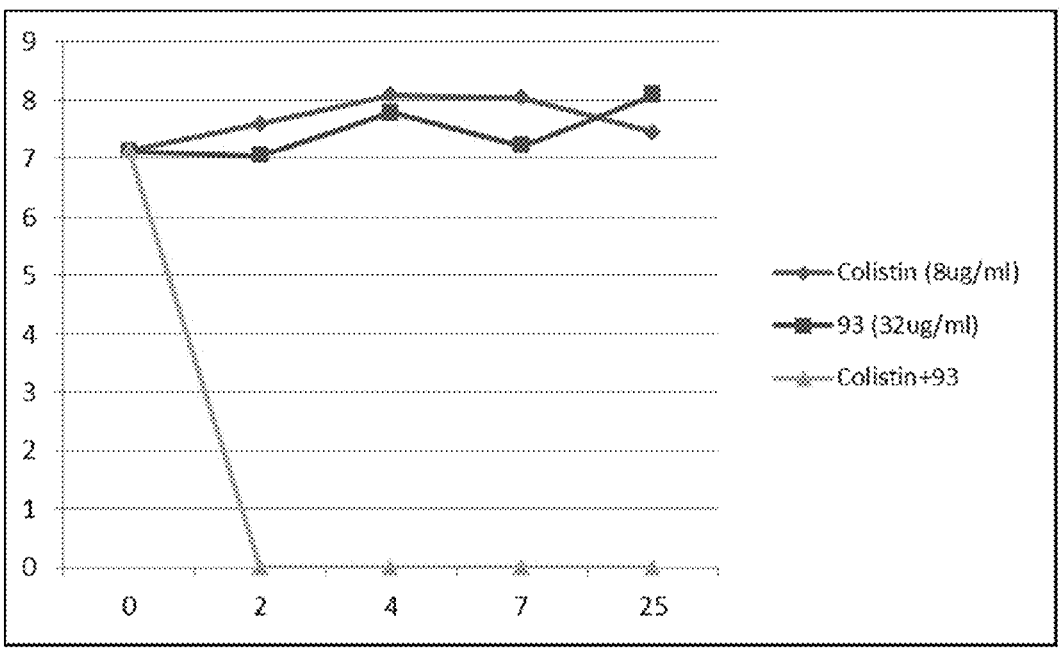
Figure 21:
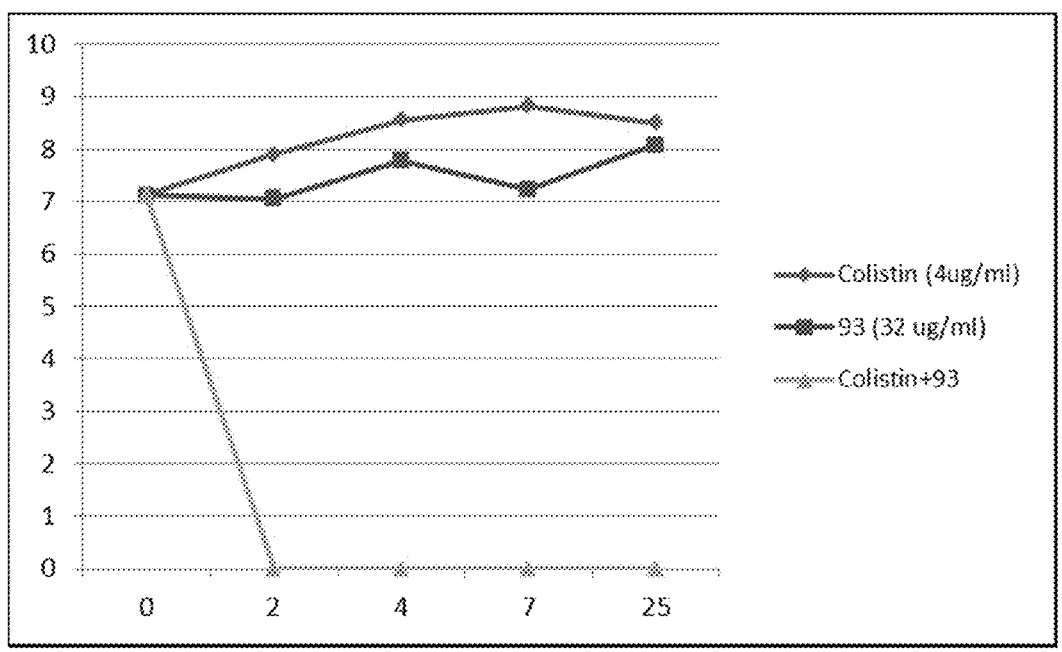
Figure 22:
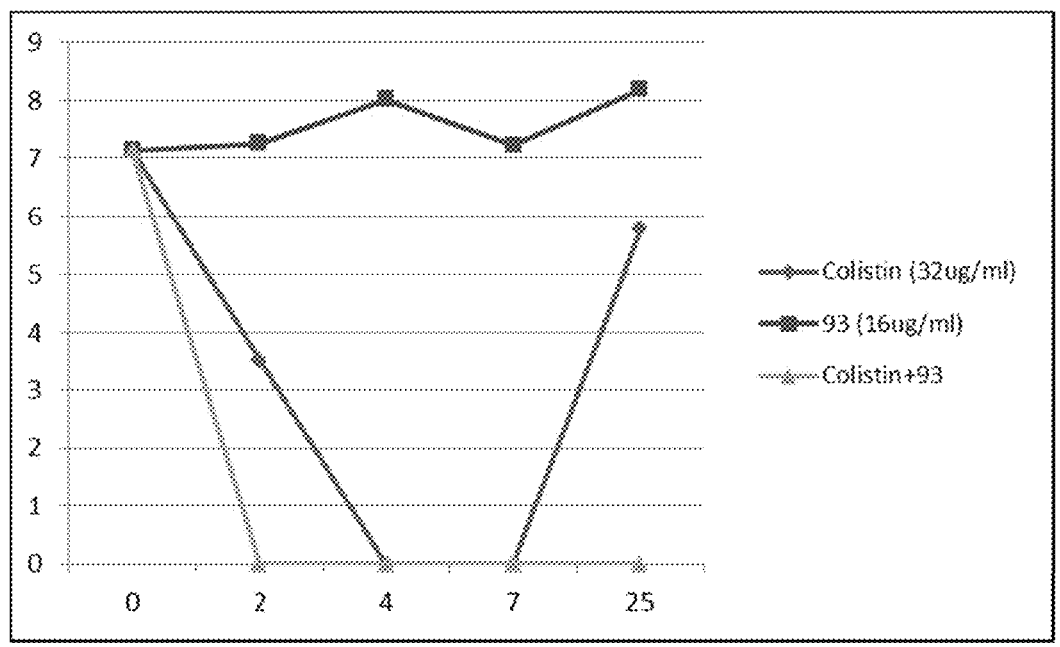
Figure 23:
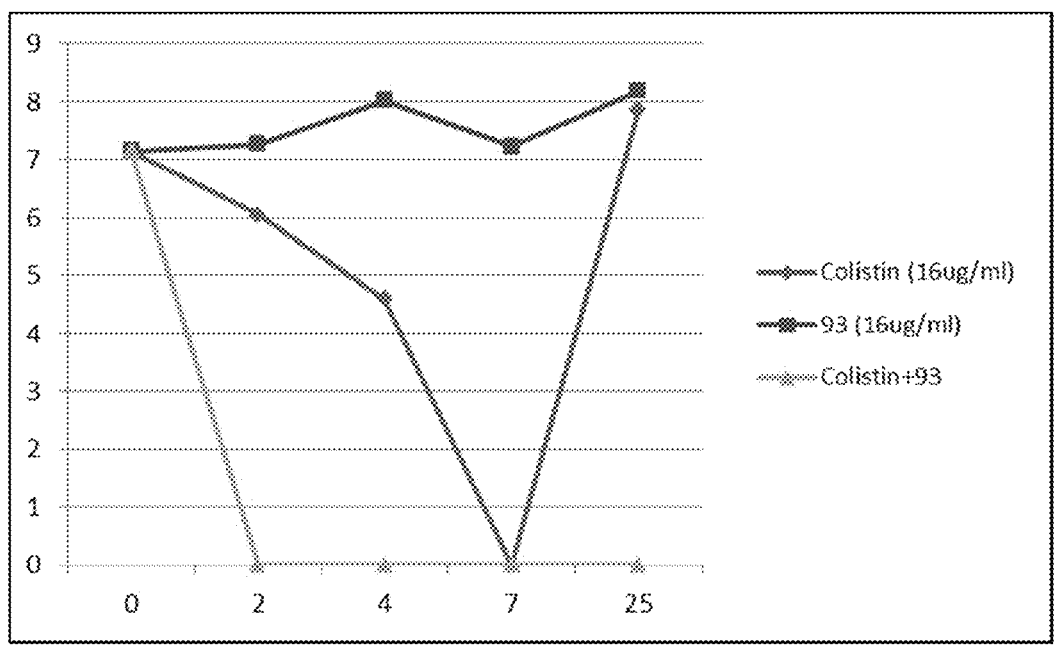
Figure 24:
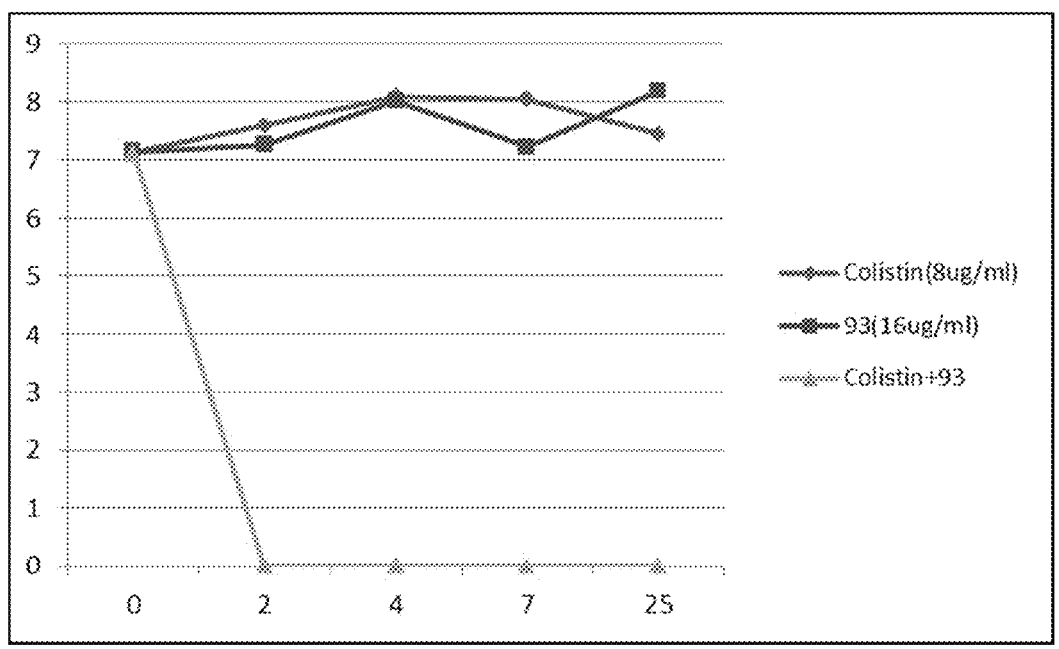
Figure 25:
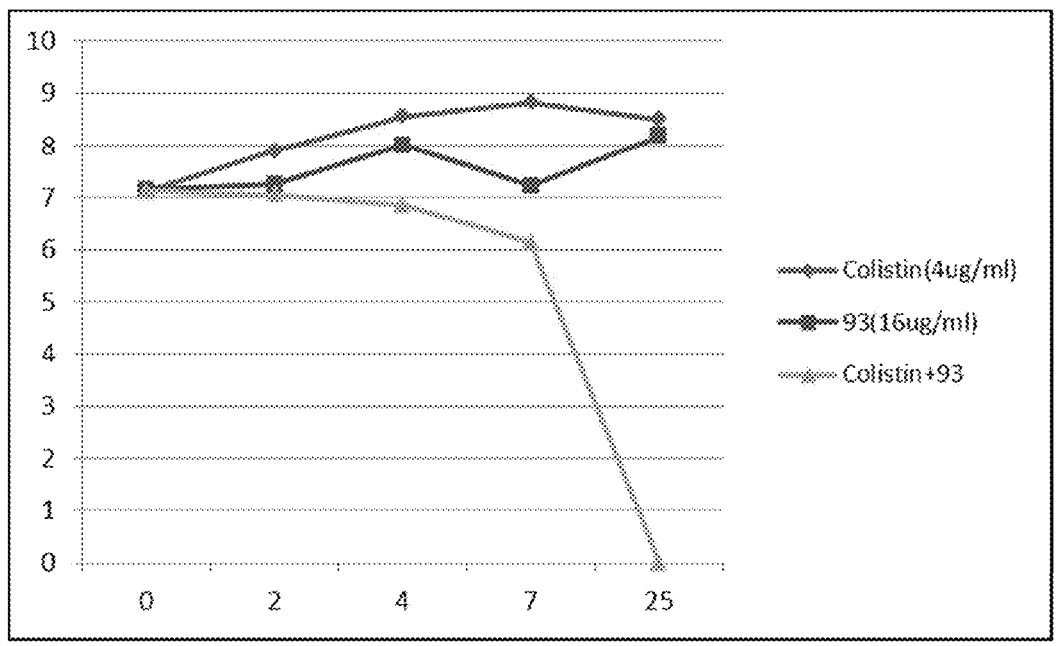
Figure 26:
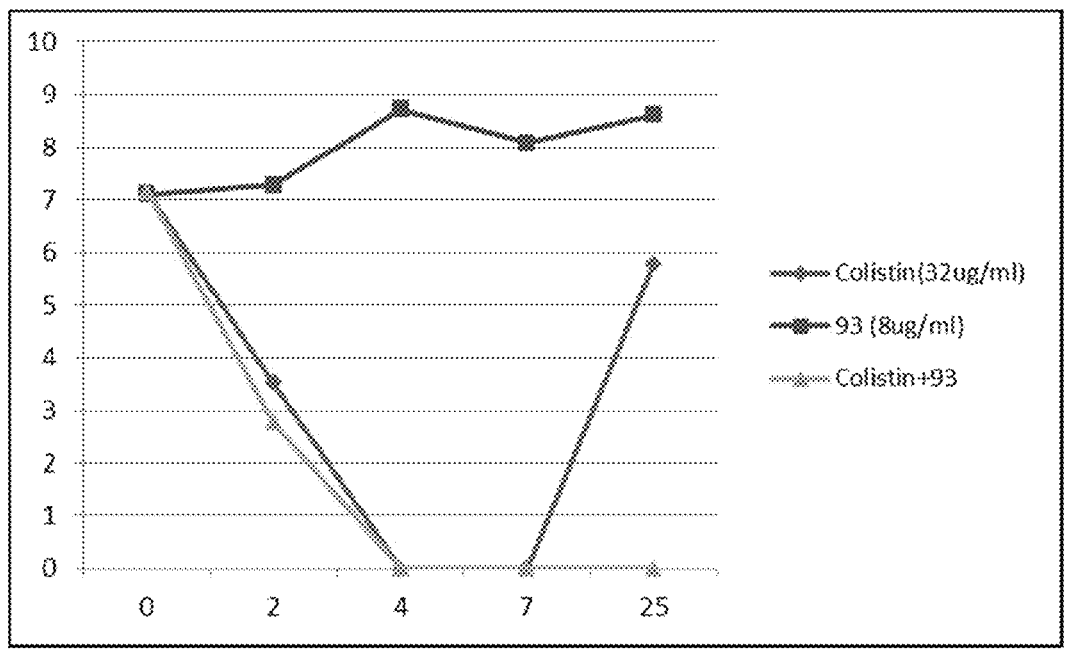
Figure 27:
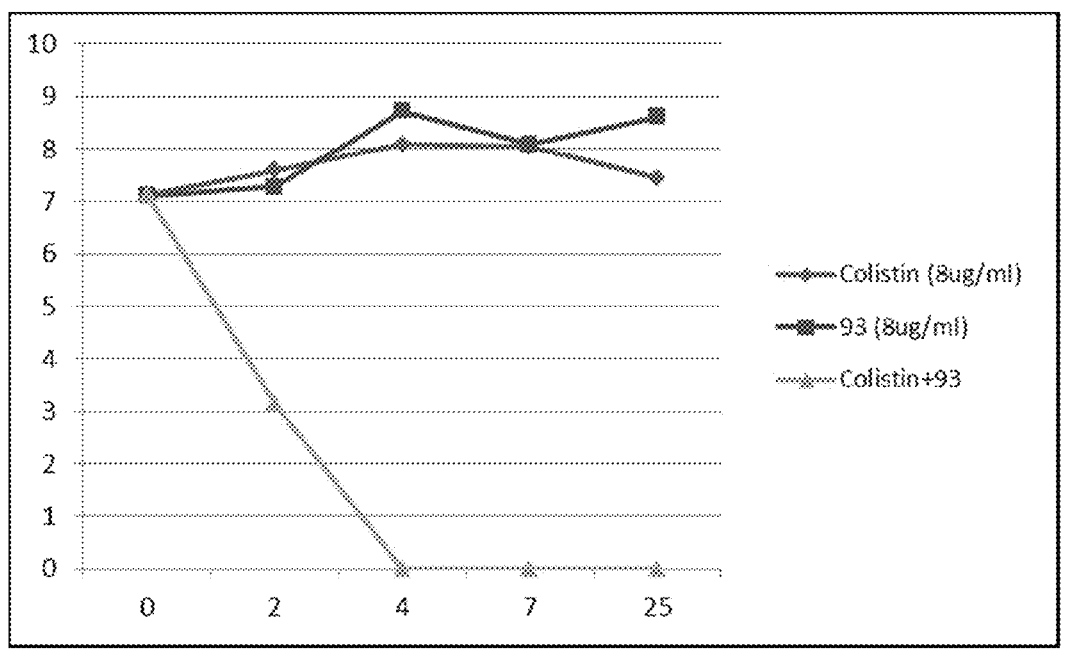
Figure 28:
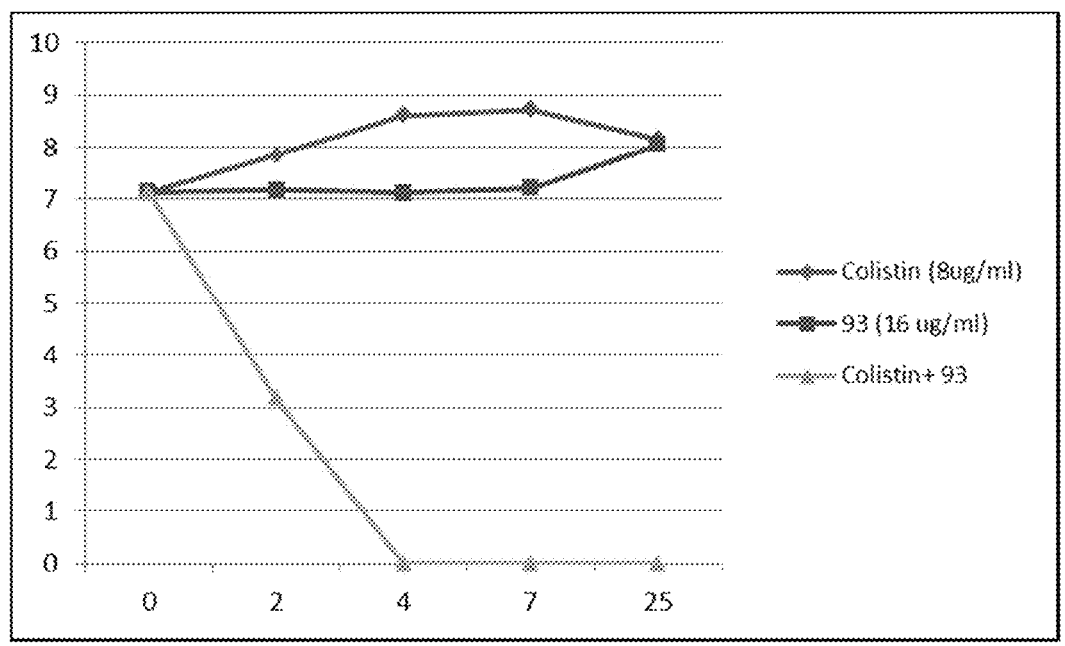
FIGS. 28-34 are time kill curves showing the combinations listed in Table 2. Suloctidil is referenced as "93".
Figure 29:
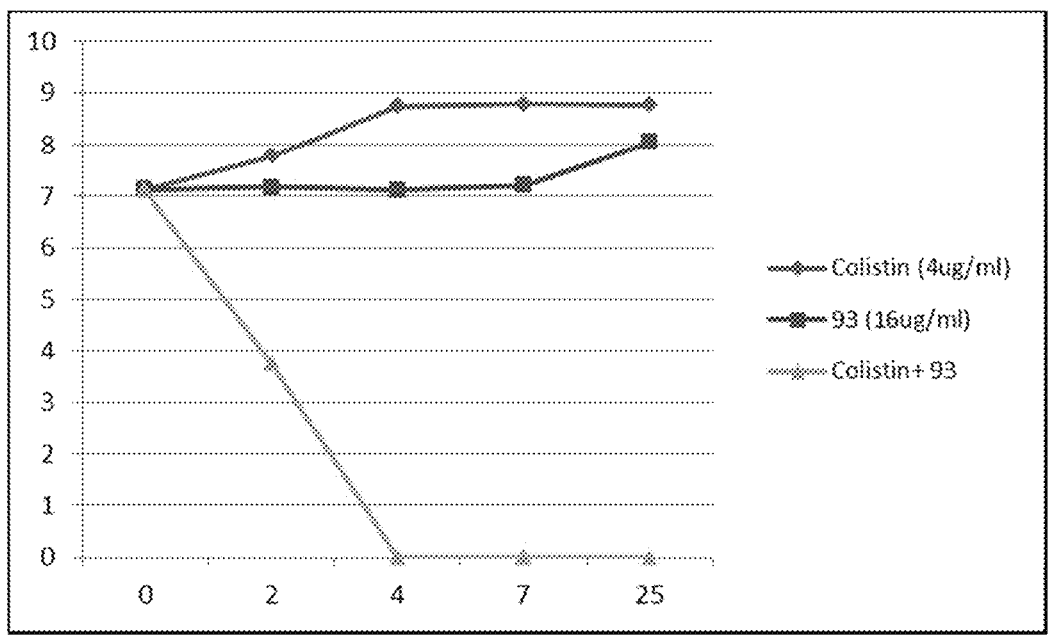
Figure 30:
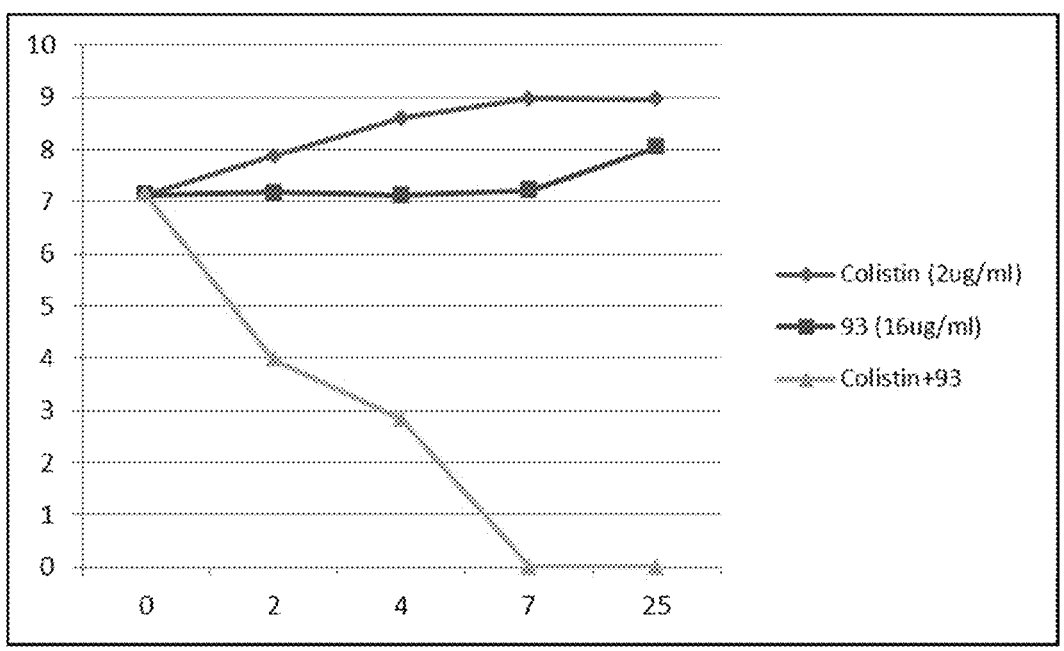
Figure 31:
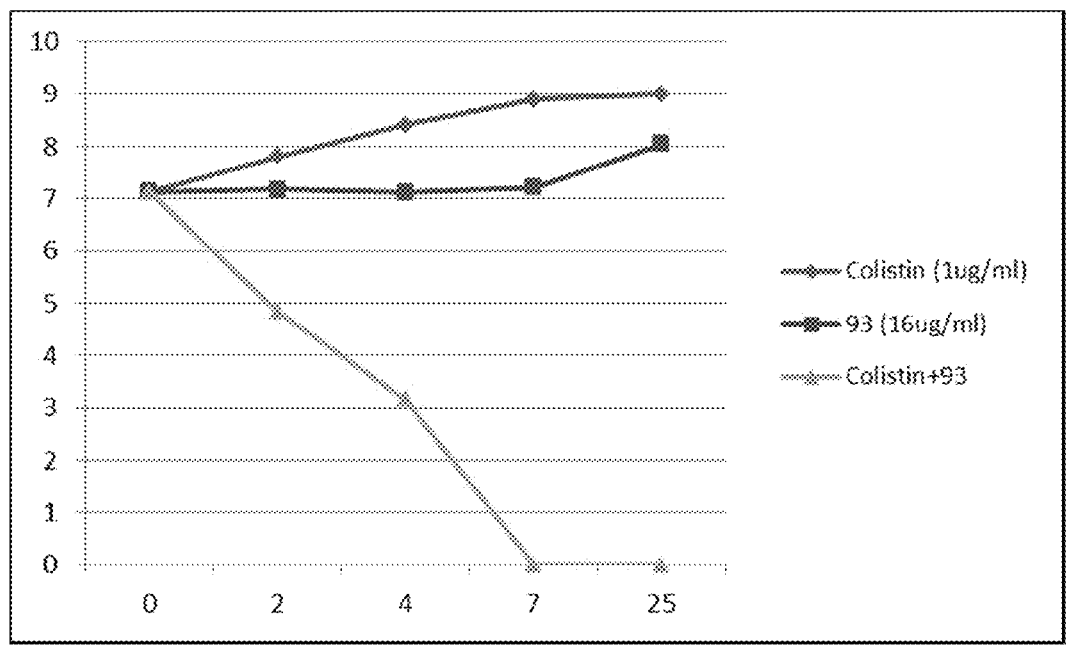
Figure 32:
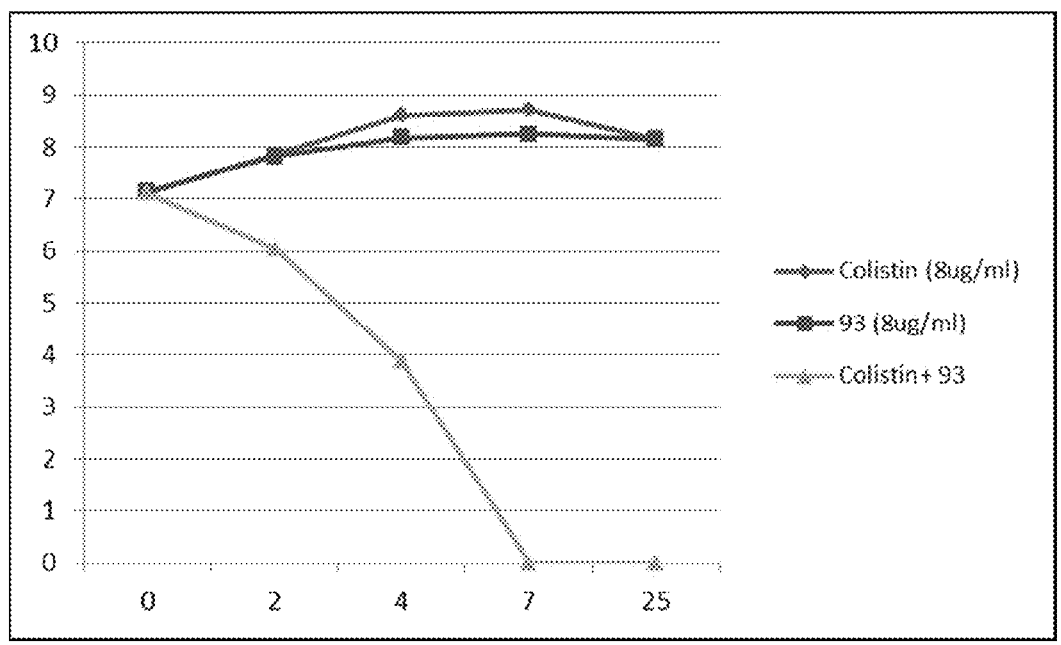
Figure 33:
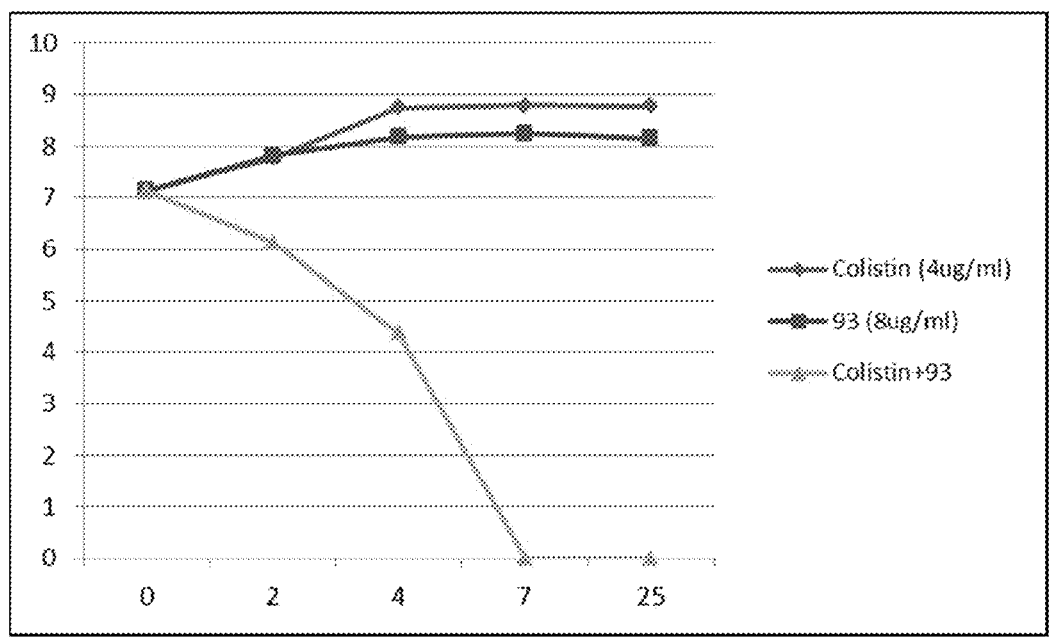
Figure 34:
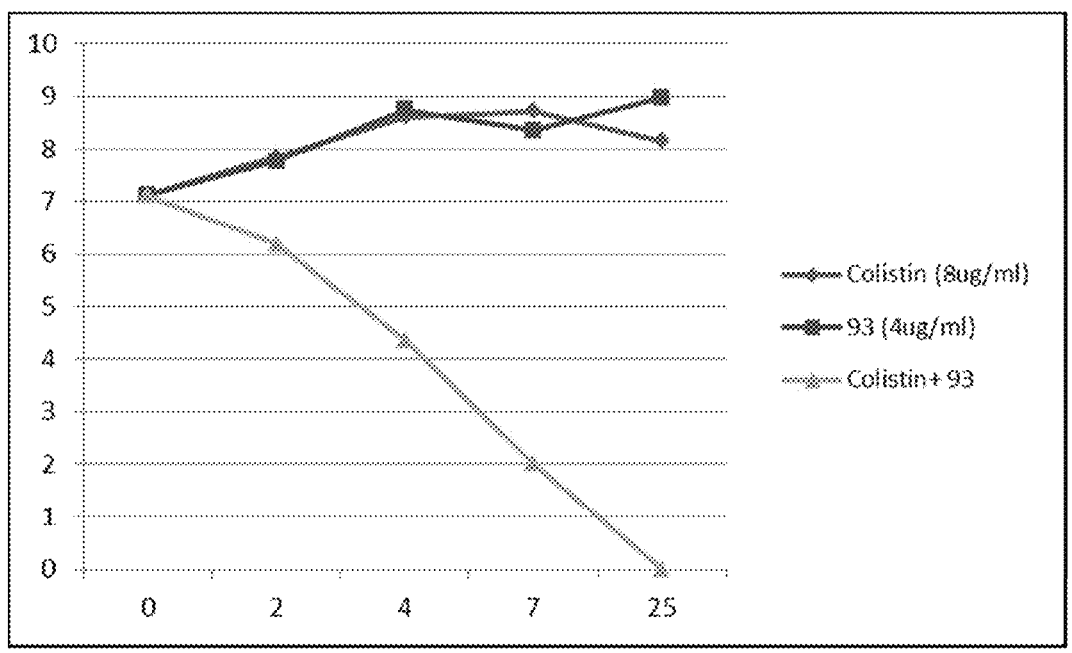

1. It can be seen from FIGS. 18 to 27 that suloctidil (i.e. "93") had no antimicrobial effect against log phase NDM-1 *K. pneumoniae* when used alone at concentrations of 32, 16, 8 and 4 µg/ml.
2. It can be seen from FIGS. 20, 21, 24, 25 and 27 that colistin also had no antimicrobial effect against log phase NDM-1 *K. pneumoniae* when used alone at concentrations of 8 and 4 µg/ml.
3. FIGS. 18, 19, 22, 23 and 26 then demonstrate that colistin had an antimicrobial effect against log phase NDM-1 *K. pneumoniae* at concentrations of 32 and 16 µg/ml, but that this effect was not long term.
4. FIG. 19 for example shows that colistin (16 µg/ml) caused complete kill after 7 hours and bacteria re-growth after 25 hours.
5. In each of FIGS. 18 to 27, it can, however, be seen that there was a significant synergistic effect against log phase NDM-1 *K. pneumoniae* when suloctidil and colistin were used in combination. This synergistic effect resulted in both a faster and longer term kill of the bacteria.

Example 4: In Vitro Synergy Effect of Suloctidil in Combination with Polymyxin E (Colistin) Against Log Phase NDM-1 *E. coli*

The synergistic effect of suloctidil in combination with colistin was tested against log phase NDM-1 *E. coli* using time-kill methods over a period of 24 hours.

Materials and Methods
Bacterial strain used: BAA2469 strain of NDM-1 *E. coli*
Growth of bacteria: Log phase growth of bacteria was carried out according to methods known in the art.
Compounds and Preparation:
(i) Suloctidil was obtained from a commercial source and dissolved in DMSO to make a stock concentration of 10 mg/ml.
(ii) Colistin was obtained from a commercial source at a concentration of 20 mg/ml.

Both suloctidil and colistin were then added to 96 well plates either alone or in the combinations shown below in Table 2.

TABLE 2

| Agent (Concentration) | Number/Letter | Combination | Combination |
|---|---|---|---|
| Colistin (8 µg/ml) | 1 | 1&A | 1&C |
| Colistin (4 µg/ml) | 2 | 2&A | 2&C |
| Colistin (2 µg/ml) | 3 | 3&A | 3&C |
| Colistin (1 µg/ml) | 4 | 4&A | 4&C |
| Suloctidil (32 µg/ml) | A | 1&B | 1&D |
| Suloctidil (16 µg/ml) | B | 2&B | 2&D |
| Suloctidil (8 µg/ml) | C | 3&B | 3&D |
| Suloctidil (4 µg/ml) | D | 4&B | 4&D |

The overnight culture was diluted with nutrient broth (Oxoid) to $10^7$ CFU/ml and 280 µl and 290 µl of the culture was added to each combination well and single agent well, respectively, to make a final concentration of 300 µl. Incubation of the compounds with the bacterial suspension was carried out for 24 hours. At 0, 2, 4, 7 and 25 hours, CFU counts were performed to measure the kill effects of the drug combination.

Results

The time-kill curves are shown in FIGS. 28 to 34, where suloctidil is referenced as "93".

Summary and Conclusion

1. It can be seen from FIGS. 28 to 34 that suloctidil (i.e. "93") had no antimicrobial effect against log phase NDM-1 *E. coli* when used alone at concentrations of 16, 8 and 4 µg/ml.
2. It can be seen from FIGS. 28 to 34 that colistin also had no antimicrobial effect against log phase NDM-1 *E. coli* when used alone at concentrations of 8, 4, 2 and 1 µg/ml.
3. In each of FIGS. 28 to 34, it can, however, be seen that there was a significant synergistic effect against log phase NDM-1 *E. coli* when suloctidil and colistin were used in combination. This synergistic effect resulted in a faster time-kill of the bacteria.

The invention claimed is:

1. A combination comprising suloctidil or a pharmaceutically acceptable derivative or prodrug thereof, and a polymyxin selected from polymyxin E and polymyxin B or a pharmaceutically acceptable derivative thereof.

2. The combination according to claim 1, wherein the polymyxin is polymyxin E or a pharmaceutically acceptable derivative thereof.

3. The combination according to claim 1 for use in the prevention and/or treatment of a microbial infection.

4. The combination according to claim 3 for use in killing multiplying, non-multiplying or clinically latent microorganisms associated with a microbial infection.

5. A pharmaceutical composition comprising suloctidil or a pharmaceutically acceptable derivative or prodrug thereof, a polymyxin selected from polymyxin E and polymyxin B or a pharmaceutically acceptable derivative thereof, and a pharmaceutically acceptable adjuvant, diluent or carrier.

6. A method of treating a microbial infection, wherein the method comprises administering to a subject in need thereof, suloctidil or a pharmaceutically acceptable derivative or prodrug thereof in combination with a polymyxin selected from polymyxin E and polymyxin B or a pharmaceutically acceptable derivative thereof.

7. The method according to claim 6, wherein the infection is a bacterial infection.

8. The method according to claim 7, wherein the microbial infection is caused by *E. coli*, Enterobacteriaceae, *Haemophilus influenzae*, Mycobacteria or *Klebsiella*.

9. The method according to claim 8 wherein the infection is caused by *E. coli* or *Klebsiella*.

10. The method according to claim 8, wherein the infection is caused by a drug-resistant strain.

11. The method according to claim 10, wherein the infection is caused by a carbapenemase-resistant strain or "extended spectrum β-lactamase" (ESPL) strain.

12. The method according to claim 6 for the treatment of tuberculosis, anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, *gardnerella* vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis, non-specific urethritis, opthalmia, osteomyelitis, otitis, orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma, Q fever, ratbite fever, reticulosis, ricin poisoning, Ritter's disease, *salmonellosis*, salpingitis, septic arthritis, septic infections, septicameia, sinusitis, skin infections, syphilis, systemic infections, tonsillitis, toxic shock syndrome, trachoma, tularaemia, typhoid, typhus, urethritis, wound infections, yaws, aspergillosis, candidiasis, cryptococcosis, favus, histoplasmosis, intertrigo, mucormycosis, tinea, onychomycosis, *pityriasis versicolor*, ringworm or sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilus influenzae, Enterococcus faecalis* or *Enterococcus faecium*.

13. A product comprising suloctidil or a pharmaceutically acceptable derivative or prodrug thereof and a polymyxin selected from polymyxin E and polymyxin B or a pharmaceutically acceptable derivative thereof, as a combined preparation for simultaneous, separate or sequential use in the treatment of a microbial infection.

14. The method according to claim 10, wherein the infection is caused by New Delhi Metallo-beta-lactamase-1 (NDM-1) resistant *Klebs. Pneumonia* or NDM-1 *E. coli*.

\* \* \* \* \*